US012320807B2

(12) United States Patent
Neto et al.

(10) Patent No.: US 12,320,807 B2
(45) Date of Patent: Jun. 3, 2025

(54) CHIMERIC PROTEIN, METHOD OF PRODUCTION AND USE THEREOF, AND ALSO A NUCLEIC ACID MOLECULE, EXPRESSION CASSETTE, EXPRESSION VECTOR, HOST CELL, COMPOSITION FOR THE DIAGNOSIS OF LEISHMANIASIS, KIT FOR THE DIAGNOSIS OF LEISHMANIASIS AND METHOD OF DIAGNOSIS OF LEISHMANIASIS IN VITRO

(71) Applicant: FUNDÃçAO OSWALDO CRUZ, Rio de Janeiro (BR)

(72) Inventors: Osvaldo Pompílio de Melo Neto, Recife (BR); Antonio Mauro Rezende, Recife (BR); Diego de Hollanda Cavalcanti Tavares, Recife (BR); Wagner José Tenório Dos Santos, Recife (BR); Artur Leonel de Castro Neto, Jabotão dos Guararapes (BR); Franklin Barbalho Magalhães, Recife (BR); Marilia Barbosa Do Nascimento, Camaragibe (BR)

(73) Assignee: FUNDÃÇAO OSWALDO CRUZ, Rio de Janeiro (BR)

( * ) Notice: Subject to any disclaimer, the term of this patent is extended or adjusted under 35 U.S.C. 154(b) by 98 days.

(21) Appl. No.: 17/433,206

(22) PCT Filed: Feb. 14, 2020

(86) PCT No.: PCT/BR2020/050044

§ 371 (c)(1),
(2) Date: Aug. 23, 2021

(87) PCT Pub. No.: WO2020/168402

PCT Pub. Date: Aug. 27, 2020

(65) Prior Publication Data

US 2022/0137046 A1 May 5, 2022

(30) Foreign Application Priority Data

Feb. 22, 2019 (BR) .......................... 1020190036397

(51) Int. Cl.
*G01N 33/569* (2006.01)
*A61K 39/008* (2006.01)
(Continued)

(52) U.S. Cl.
CPC ......... *G01N 33/569* (2013.01); *A61K 39/008* (2013.01); *C07K 14/44* (2013.01);
(Continued)

(58) Field of Classification Search
CPC ........... G01N 33/569; G01N 33/56905; G01N 2469/20; A61K 39/008; C07K 14/44;
(Continued)

(56) References Cited

FOREIGN PATENT DOCUMENTS

WO 2010108245 A2 9/2010

OTHER PUBLICATIONS

International Search Report and Written Opinion w English Translation of the ISR for PCT/BR2020/050044 dated Mar. 4, 2020.
(Continued)

*Primary Examiner* — Joanne Hama
*Assistant Examiner* — Audrey L Buttice
(74) *Attorney, Agent, or Firm* — Hahn Loeser & Parks, LLP; John J. Cunniff

(57) ABSTRACT

The present invention relates to chimeric proteins, their uses and production method comprising native protein fractions from *Leishmania infantum* for the Visceral Leishmaniasis diagnosis. The invention also relates to nucleic acid, expression cassette, expression vector, host cell, visceral leishma-
(Continued)

niasis diagnostic kit, visceral leishmaniasis diagnostic kit, visceral leishmaniasis diagnostic method, and vaccine composition.

16 Claims, 5 Drawing Sheets

Specification includes a Sequence Listing.

(51) Int. Cl.
*C07K 14/44* (2006.01)
*C12N 15/63* (2006.01)
(52) U.S. Cl.
CPC .......... *C12N 15/63* (2013.01); *C07K 2317/24* (2013.01); *G01N 2469/20* (2013.01)
(58) Field of Classification Search
CPC ............ C07K 2317/24; C07K 2319/00; C07K 2319/21; C12N 15/63; C12N 15/70; Y02A 50/30
See application file for complete search history.

(56) References Cited

OTHER PUBLICATIONS

Dias, D. S. et al. Vaccination with a CD4+ and CD8+ T-cell epitopes-based recombinant chimeric protein derived from Leishmania infantum proteins confers protective immunity against visceral leishmaniasis. Transl Res. 2018. vol. 200, pp. 18-34. doi: 10.1016/j.trsl.2018.05.001.
Kaye, P.; Scott, P. Leishmaniasis: complexity at the host-pathogen interface. Nature reviews. Microbiology, v. 9, n. 8, p. 604-615, 2011.
Murray, H. W. et al. Advances in leishmaniasis. Lancet, vol. 366, n. 1474-547X (Electronic), p. 1561-1577, Oct. 2005.
Akhoundi et al., A Historical Overview of the Classification, Evolution, and Dispersion of Leishmania Parasites and Sandflies. PLoS Neglected Tropical Diseases, v. 10, n. 3, p. 1-40, 2016.
Ready, P. D. Biology of Phlebotomine Sand Flies as Vectors of Disease Agents. Annual Review of Entomology, v. 58, n. 1, p. 227-250, 2013.
Kamhawi, S. Phlebotomine sand flies and Leishmania parasites: friends or foes? Trends in Parasitology, v. 22, n. 9, p. 439-445, 2006.
Alvar, J. et al. Leishmaniasis worldwide and global estimates of its incidence. PLoS ONE, v. 7, n. 5, 2012.
Chappuis, F. et al. Visceral leishmaniasis: what are the needs for diagnosis, treatment and control? Nat.Rev. Microbiol., V. 5, n. 1740-1534 (Electronic), p. 873-882, Nov. 2007.
Quinnell, R. J .; Courtenay, O. Transmission, reservoir hosts and control of visceral zoonotic leishmaniasis. Parasitology, v. 136, n. 14, p. 1915, 2009.
Srivastava, S. et al. Possibilities and challenges for developing a successful vaccine for leishmaniasis. Parasites & Vectors, v. 9, n. 1, p. 277, 2016.
Singh, O. P.; Sundar, S. Developments in Diagnosis of Visceral Leishmaniasis in the Elimination Era. V. 2015, 2015.
Srividya, G. et al. Diagnosis of visceral leishmaniasis: developments over the last decade. ParasitoLRes., V. 110, n. 1432-1955 (Electronic), p. 1065-1078, sea. 2012.
Gomes, YM et al. Diagnosis of canine visceral leishmaniasis: Biotechnological advances. Veterinary Journal, vol. 175, n. 1, p. 45-52, 2008.
Noli, C.; Saridomichelakis, M. N. An update on the diagnosis and treatment of canine leishmaniosis caused by Leishmania infantum (syn. L. chagasi). The Veterinary Journal, vol. 202, n. 3, p. 425-435, 2014.
Paltrinieri, S. et al. Laboratory tests for diagnosing and monitoring canine leishmaniasis. Veterinary Clinicai Pathology, vol. 45, n. 4, p. 552-578, 2016.
Saridomichelakis, M. N. Advances in the pathogenesis of canine leishmaniosis: Epidemiologic and diagnostic implications. Veterinary Dermatology, v. 20, n. 5-6, p. 471-489, 2009.
Srivastava, P. et al. Diagnosis of visceral leishmaniasis. Trans.R. Soc.Trop.Med.Hyg., V. 105, n. 1878-3503 (Electronic), p. 1-6, Jan. 2011.
Sundar, S.; Rai, M. Laboratory diagnosis of visceral leishmaniasis. Clin.Diagn.Lab Immunol., V. 9, n. 1071-412X (Print), p. 951-958, set. 2002.
De Ruiter, C. M. et al. Molecular tools for diagnosis of visceral leishmaniasis: systematic review and meta-analysis of diagnostic test accuracy. J.Clin.Microbiol., V. 52, n. 1098-660X (Electronic), p. 3147-3155, set. 2014.
Sundar, S. et al. Rapid accurate field diagnosis of Indian visceral leishmaniasis. Lancet, vol. 351, n. 9102, p. 563-565, 1998.
Chappuis, F. et al. A meta-analysis of the diagnostic performance of the direct agglutination test and rK39 dipstick for visceral leishmaniasis. BMJ (Clinical research ed.), V. 333, n. 7571, p. 723, 2006.
Boelaert, M. et al. A comparative study of the effectiveness of diagnostic tests for visceral leishmaniasis. Am.J.Trop.Med.Hyg., V. 70, n. 1, p. 72-77, Jan. 2004.
Quinnell, R. J. et al. Evaluation of rK39 rapid diagnostic tests for canine visceral leishmaniasis: longitudinal study and meta-analysis. PLoS.Negl.Trop.Dis., V. 7, n. 1935-2735 (Electronic), p. el992, 2013.
Pattabhi, S. et al. Design, development and evaluation of rK28-based point-of-care tests for improving rapid diagnosis of visceral leishmaniasis. PLoS Neglected Tropical Diseases, v. 4, n. 9, 2010.
Fraga, D. B. M. et al. The Rapid Test Based on Leishmania infantum Chimeric rK28 Protein Improves the Diagnosis pf Canine Visceral Leishmaniasis by Reducing the Detection of False-Positive Dogs. PLoS Neglected Tropical Diseases, v. 10, n. 1, p. 1-11, 2016.
Oliveira, G. G. et al. Characterization of novel Leishmania infantum recombinant proteins encoded by genes from five families with distinct capacities for serodiagnosis of canine and human visceral leishmaniasis. Am.J.Trop.Med.Hyg., V. 85, n. 1476-1645 (Electronic), p. 1025-1034, ten. 2011.
Magalhães, F. B. et al. Evaluation of a new set of recombinant antigens for the serological diagnosis of human and canine visceral leishmaniasis. PLoS ONE, v. 12, n. 9, p. e0184867, 2017.
Fraga, D. B. M. et al. A multicentric evaluation of the recombinant Leishmania infantum antigen-based immunochromatographic assay for the serodiagnosis of canine visceral leishmaniasis. Parasit. Vectors., V. 7, n. 1756-3305 (Electronic), p. 136, 2014.
Peixoto, H. M .; De Oliveira, M. R. F.; Romero, G. A. S. Serological diagnosis of canine visceral leishmaniasis in Brazil: systematic review and meta-analy sis. Tropical Medicine & International Health, vol. 20, n. 3, p. 334-352, 2015.
Bourdeau, P. et al. Management of canine leishmaniosis in endemic SW European regions: a questionnaire-based multinational survey. Parasites & Vectors, v. 7, n. 1, p. 110, 2014.
Camussone, C. et al. Comparison of recombinant Trypanosoma cruzi peptide mixtures versus multiepitope chimeric proteins as sensitizing antigens for immunodiagnosis. Clinic and Vaccine Immunology, v. 16, n. 6, p. 899-905, 2009.
Boarino, A. et al. Development of Recombinant Chimeric Antigen Expressing Immunodominant B Epitopes of Leishmania infantum for Serodiagnosis of Visceral Leishmaniasis. Clinic and Vaccine Immunology, v. 12, n. 5, p. 647-653, 2005.
Faria, A. R. et al. Novel Recombinant Multiepitope Proteins for the Diagnosis of Asymptomatic Leishmania infantum-infected Dogs. PLoS Neglected Tropical Diseases, v. 9, n. 1, p. 13-16, 2015.
Soto, M. et al. Multicomponent chimeric antigen for serodiagnosis of canine visceral leishmaniasis. Journal of Clinical Microbiology, vol. 36, n. 1, p. 58-63, 1998.
El-Manzalawy, Y .; Dobbs, D .; Honavar, V. Predicting linear B-cell epitopes using string kemels. Journal of Molecular Recognition, v. 21, n. 4, p. 243-255, Jul. 2008.
Barrouin-Melo, S. M. et al. Can spleen aspirations be safely used for the parasitological diagnosis of canine visceral leishmaniosis? A study on assymptomatic and polysymptomatic animals. Veterinary Journal, vol. 171, n. 2, p. 331-339, 2006.

(56) References Cited

OTHER PUBLICATIONS

Boelaert, M. et al. Rapid tests for the diagnosis of visceral leishmaniasis in patients with suspected disease. Cochrane.Database.Syst.Rev., V. 6, n. 1469-493X (Electronic), p. CD009135, 2014.
Campos, R. M. et al. Distinct mitochondrial HSP70 homologues conserved in various Leishmania species suggest novel biological functions. Molecular and Biochemical Parasitology, v. 160, n. 2, p. 157-162, 2008.
Canavate, C. et al. Evaluation of two rK39 dipstick tests, direct agglutination test, and indirect fluorescent antibody test for diagnosis of visceral leishmaniasis in a new epidemic site in highland Ethiopia. American Journal of Tropical Medicine and Hygiene, v. 84, n. 1, p. 102-106, 2011.
Mettler, M. et al. Evaluation of enzyme-linked immunosorbent assays, an immunofluorescent-antibody test, and two rapid tests (immunochromatographic-dipstick and gel tests) for serological diagnosis of symptomatic and asymptomatic Leishmania infections in dogs. J.Clin.Microbiol., V. 43, n. 0095-1137 (Print), p. 5515-5519, Nov. 2005.
Pace, D. Leishmaniasis. Journal of Infection, v. 69, n. Ps, p. S10-S18, 2014.
Singh, S. et al. Diagnostic and prognostic value of K39 recombinant antigen in Indian leishmaniasis. J. Parasitol., V. 81, n. 0022-3395 (Print), p. 1000-1003, ten. 1995.
Santos, W.J.T. Optimization of conditions for overexpression in *Escherichia coli* of chimeric proteins with potential for diagnosis of visceral leishmaniasis, Federal University of Pernambuco Center for Biological Sciences Postgraduate Program in Genetics, 2015.
Welch, M. et al. Designing genes for successful protein expression. 1. ed. [s.l.] Elsevier Inc., 2011. v. 498.

SEQUENCE LISTING

<160> NUMBER OF SEQ ID NOS: 8

<210> SEQ ID NO 1
<211> LENGTH: 2823
<212> TYPE: DNA
<213> ORGANISM: Leishmania infantum

<400> SEQUENCE: 1
atggcaaaaa aactgctgtt cgcgattccg ctggtggtgc cgttctatag ccataccatg 60
gctagcatga ctggtggaca gcaaatgggt cggatgatcg aggccgagga acaggccagg 120
agggaggctg aagagcaggc cagacgcgtc gccgaggaac aggccaggag ggaggcagag 180
gagcaagcca ggagagaggt cgagcttgaa gagaaactga ggggaactga agccagagct 240
gccgaactcg ccgccaggct gaaggccatt gctgccatga aagcaagcat ggtgcaggaa 300
agggagtccg cacgcgacgc actggaagaa aagctgaggg gcagcgaggt gagggccgca 360
gagctcgcag ccagactcaa agccgcagtg gcagccaaaa gcagcgcaga acaggataga 420
gaaaacacga gagccaccct ggaacagaga ctgagggaga gtgaggaaag ggccgcagag 480
ctggccagtc agctggaagc agccgcagcc gcaaagagca gcgcagagca ggacagggaa 540
aacacacgag cagccctgga ggaaaagctg aggggatcag aggagagggc tgcagagctg 600
ggcacccgag tcaaggccag cagcgccgca aaggcccttg ccgagcagga acgcgatagg 660
attagggctg ctttggaaga gaaactgagg gatagcgagg ccagagctgc cgaactgacc 720
accaagctgg aggccactgt ggccgccaaa tcaagtgccg agcaagagag agagaacatc 780
aaagtggcag tcgaggccac tgagctggag agagcccagg aagaggctga aaggctggca 840
ggcgacctgg agaaagctga ggaggaggca gaaagactgg caggcgacct ggaaaaagcc 900
caagaggaag ctgagacgct ggctggcgtc aacgagctgg ctgacaagga cccagaattg 960
gccgccttta gggaaaagcg cagggccgct cacggagcca gagcagacga acccgagctg 1020
gctgctgccg acgggattag cacacgcaat gccagggccg gaagccgtgg acgtccagcc 1080
gcacagatca atcccgctgc tgaagccgtg gatcccgtga ctatcgcagc tgagccactg 1140
tacgccgtga ccctcgacga atacaaggcc aaacagaccg cactggaaaa cgcagttgaa 1200
gtggcctgcg cagccgaaga gactgtgaaa gagaaactga gggagaacag cgacctgatg 1260
gtggagctgg aaaaggtgcg tgaccaggct tacgagatgg ataggaggag gcaagaagac 1320

-continued

```
ggagccgcaa tggaagggga gctgctggtt gtgctgatgg agctcaagaa actcaaggga   1380

atcaacgacg ccctgctggc tgtgcttagg gacaaagagt gtgaggtgaa agagcttcga   1440

taccacaacg agttgtgggt tgacccaacg ggagacaaga agcaggtggt gacgaggcac   1500

actaagatct ttgacggcaa ctgggagagg attgtgcgag aacgacccga agggctgttc   1560

gcagcctttg tgatcgatag cagtaacgcc tgccacgtcc ctggggacaa catcaaacag   1620

gtgtcttttg accacgacgt cgacatggca ctgcagaggg ttcgtgaagc agcagaaaaa   1680

gcgaaatgcg aattaagcag tgcgatggaa acagaagtta atttaccatt tattaccgct   1740

aacgcagatg gcgcgcaaca tatccagatg cgcatttctc gttctaaatt cgaaggtatc   1800

acccagaggt tgattgatcg ttcaatcgcc ccgtgtaaac agtgtatgaa ggatgcaggg   1860

gttgagctca aagaaattaa tgatgttgtg cttgttggcg ggatgacaag aatgccaaaa   1920

gttgttgaag aagtaaaaaa gtttttttcaa aaagatccct ttcgcggcgt gaatcccgac   1980

gaggccgtcg ctcttggtgc ggccaccctg ggcggagttc tgcgtggtga tgtcaagggt   2040

ttagtgttgc tggatgtgac acctttgtca ctgggaattg agactctggg tggtgtcttt   2100

actcgtatga taccgaaaaa cactaccatt cccacgaaaa agtcgcagac cttttctact   2160

gctgccgaca atcagacaca ggtcggaatt aaggtttttc aaggtgagcg tgaaatggct   2220

gctgacaacc agatgatggg gcagttcgac ctggttggga ttccgcccgc acctaggggg   2280

gtgccccaaa tcgaagttac cttcgacata gacgccaatg gtatctgtca tgtcacagca   2340

aaagataaag caacgggtaa aacacagaat attacgatca cagcaaacgg aggattgagt   2400

aaagagcaga ttgaacagat gattcgcgat tcggaacaac atgctgaggc cgatcgtgtc   2460

aagcgtgaac tggtcgaggt tagaaataat gcggagaccc agcttaccac cgcggaacgt   2520

caattaggtg aatggaagta tgtttccgat gcagaaaagg agaatgtaaa aacgctggtc   2580

gccgagttgc gtaaggcaat ggaaaatcca aatgttgcga aagacgatct ggctgcagca   2640

acagacaaac tacaaaaggc cgtaatggaa tgcggcagaa ccgagtatca gcaagccgcc   2700

gctgctaaca gcggctctac gtcgaatagc ggtgaacaac agcagcaaca aggccaggga   2760

gaacaacagc aacagcagtc tcagggagag gaaacaaaac tcgagcatca tcatcatcat   2820

cat                                                                 2823
```

<210> SEQ ID NO 2
<211> LENGTH: 941
<212> TYPE: PRT
<213> ORGANISM: Leishmania infantum

<400> SEQUENCE: 2

```
Met Ala Lys Lys Leu Leu Phe Ala Ile Pro Leu Val Val Pro Phe Tyr
1               5                   10                  15

Ser His Thr Met Ala Ser Met Thr Gly Gly Gln Gln Met Gly Arg Met
            20                  25                  30

Ile Glu Ala Glu Glu Gln Ala Arg Arg Glu Ala Glu Glu Gln Ala Arg
        35                  40                  45

Arg Val Ala Glu Glu Gln Ala Arg Arg Glu Ala Glu Glu Gln Ala Arg
    50                  55                  60

Arg Glu Val Glu Leu Glu Glu Lys Leu Arg Gly Thr Glu Ala Arg Ala
65                  70                  75                  80

Ala Glu Leu Ala Ala Arg Leu Lys Ala Ile Ala Ala Met Lys Ala Ser
                85                  90                  95
```

-continued

```
Met Val Gln Glu Arg Glu Ser Ala Arg Asp Ala Leu Glu Glu Lys Leu
            100                 105                 110

Arg Gly Ser Glu Val Arg Ala Ala Glu Leu Ala Ala Arg Leu Lys Ala
        115                 120                 125

Ala Val Ala Ala Lys Ser Ser Ala Glu Gln Asp Arg Glu Asn Thr Arg
    130                 135                 140

Ala Thr Leu Glu Gln Arg Leu Arg Glu Ser Glu Glu Arg Ala Ala Glu
145                 150                 155                 160

Leu Ala Ser Gln Leu Glu Ala Ala Ala Ala Ala Lys Ser Ser Ala Glu
                165                 170                 175

Gln Asp Arg Glu Asn Thr Arg Ala Ala Leu Glu Glu Lys Leu Arg Gly
            180                 185                 190

Ser Glu Glu Arg Ala Ala Glu Leu Gly Thr Arg Val Lys Ala Ser Ser
        195                 200                 205

Ala Ala Lys Ala Leu Ala Glu Gln Glu Arg Asp Arg Ile Arg Ala Ala
    210                 215                 220

Leu Glu Glu Lys Leu Arg Asp Ser Glu Ala Arg Ala Ala Glu Leu Thr
225                 230                 235                 240

Thr Lys Leu Glu Ala Thr Val Ala Ala Lys Ser Ser Ala Glu Gln Glu
                245                 250                 255

Arg Glu Asn Ile Lys Val Ala Val Glu Ala Thr Glu Leu Glu Arg Ala
            260                 265                 270

Gln Glu Glu Ala Glu Arg Leu Ala Gly Asp Leu Glu Lys Ala Glu Glu
        275                 280                 285

Glu Ala Glu Arg Leu Ala Gly Asp Leu Glu Lys Ala Gln Glu Glu Ala
    290                 295                 300

Glu Thr Leu Ala Gly Val Asn Glu Leu Ala Asp Lys Asp Pro Glu Leu
305                 310                 315                 320

Ala Ala Phe Arg Glu Lys Arg Arg Ala Ala His Gly Ala Arg Ala Asp
                325                 330                 335

Glu Pro Glu Leu Ala Ala Ala Asp Gly Ile Ser Thr Arg Asn Ala Arg
            340                 345                 350

Ala Gly Ser Arg Gly Arg Pro Ala Ala Gln Ile Asn Pro Ala Ala Glu
        355                 360                 365

Ala Val Asp Pro Val Thr Ile Ala Ala Glu Pro Leu Tyr Ala Val Thr
    370                 375                 380

Leu Asp Glu Tyr Lys Ala Lys Gln Thr Ala Leu Glu Asn Ala Val Glu
385                 390                 395                 400

Val Ala Cys Ala Ala Glu Glu Thr Val Lys Glu Lys Leu Arg Glu Asn
                405                 410                 415

Ser Asp Leu Met Val Glu Leu Glu Lys Val Arg Asp Gln Ala Tyr Glu
            420                 425                 430

Met Asp Arg Arg Arg Gln Glu Asp Gly Ala Ala Met Glu Gly Glu Leu
        435                 440                 445

Leu Val Val Leu Met Glu Leu Lys Lys Leu Lys Gly Ile Asn Asp Ala
    450                 455                 460

Leu Leu Ala Val Leu Arg Asp Lys Glu Cys Glu Val Lys Glu Leu Arg
465                 470                 475                 480

Tyr His Asn Glu Leu Trp Val Asp Pro Thr Gly Asp Lys Lys Gln Val
                485                 490                 495

Val Thr Arg His Thr Lys Ile Phe Asp Gly Asn Trp Glu Arg Ile Val
            500                 505                 510

Arg Glu Arg Pro Glu Gly Leu Phe Ala Ala Phe Val Ile Asp Ser Ser
```

-continued

```
        515                 520                 525

Asn Ala Cys His Val Pro Gly Asp Asn Ile Lys Gln Val Ser Phe Asp
    530                 535                 540

His Asp Val Asp Met Ala Leu Gln Arg Val Arg Glu Ala Ala Glu Lys
545                 550                 555                 560

Ala Lys Cys Glu Leu Ser Ser Ala Met Glu Thr Glu Val Asn Leu Pro
                565                 570                 575

Phe Ile Thr Ala Asn Ala Asp Gly Ala Gln His Ile Gln Met Arg Ile
            580                 585                 590

Ser Arg Ser Lys Phe Glu Gly Ile Thr Gln Arg Leu Ile Asp Arg Ser
        595                 600                 605

Ile Ala Pro Cys Lys Gln Cys Met Lys Asp Ala Gly Val Glu Leu Lys
    610                 615                 620

Glu Ile Asn Asp Val Val Leu Val Gly Gly Met Thr Arg Met Pro Lys
625                 630                 635                 640

Val Val Glu Glu Val Lys Lys Phe Phe Gln Lys Asp Pro Phe Arg Gly
                645                 650                 655

Val Asn Pro Asp Glu Ala Val Ala Leu Gly Ala Ala Thr Leu Gly Gly
            660                 665                 670

Val Leu Arg Gly Asp Val Lys Gly Leu Val Leu Leu Asp Val Thr Pro
        675                 680                 685

Leu Ser Leu Gly Ile Glu Thr Leu Gly Gly Val Phe Thr Arg Met Ile
    690                 695                 700

Pro Lys Asn Thr Thr Ile Pro Thr Lys Lys Ser Gln Thr Phe Ser Thr
705                 710                 715                 720

Ala Ala Asp Asn Gln Thr Gln Val Gly Ile Lys Val Phe Gln Gly Glu
                725                 730                 735

Arg Glu Met Ala Ala Asp Asn Gln Met Met Gly Gln Phe Asp Leu Val
            740                 745                 750

Gly Ile Pro Pro Ala Pro Arg Gly Val Pro Gln Ile Glu Val Thr Phe
        755                 760                 765

Asp Ile Asp Ala Asn Gly Ile Cys His Val Thr Ala Lys Asp Lys Ala
    770                 775                 780

Thr Gly Lys Thr Gln Asn Ile Thr Ile Thr Ala Asn Gly Gly Leu Ser
785                 790                 795                 800

Lys Glu Gln Ile Glu Gln Met Ile Arg Asp Ser Glu Gln His Ala Glu
                805                 810                 815

Ala Asp Arg Val Lys Arg Glu Leu Val Glu Val Arg Asn Asn Ala Glu
            820                 825                 830

Thr Gln Leu Thr Thr Ala Glu Arg Gln Leu Gly Glu Trp Lys Tyr Val
        835                 840                 845

Ser Asp Ala Glu Lys Glu Asn Val Lys Thr Leu Val Ala Glu Leu Arg
    850                 855                 860

Lys Ala Met Glu Asn Pro Asn Val Ala Lys Asp Asp Leu Ala Ala Ala
865                 870                 875                 880

Thr Asp Lys Leu Gln Lys Ala Val Met Glu Cys Gly Arg Thr Glu Tyr
                885                 890                 895

Gln Gln Ala Ala Ala Ala Asn Ser Gly Ser Thr Ser Asn Ser Gly Glu
            900                 905                 910

Gln Gln Gln Gln Gln Gly Gln Gly Glu Gln Gln Gln Gln Gln Ser Gln
        915                 920                 925

Gly Glu Glu Thr Lys Leu Glu His His His His His His
    930                 935                 940
```

<210> SEQ ID NO 3
<211> LENGTH: 2766
<212> TYPE: DNA
<213> ORGANISM: Leishmania infantum

<400> SEQUENCE: 3
atggctagca tgactggtgg acagcaaatg ggtcggatga tcgaggccga ggaacaggcc 60
aggagggagg ctgaagagca ggccagacgc gtcgccgagg aacaggccag gagggaggca 120
gaggagcaag ccaggagaga ggtcgagctt gaagagaaac tgaggggaac tgaagccaga 180
gctgccgaac tcgccgccag gctgaaggcc attgctgcca tgaaagcaag catggtgcag 240
gaaagggagt ccgcacgcga cgcactggaa gaaaagctga ggggcagcga ggtgagggcc 300
gcagagctcg cagccagact caaagccgca gtggcagcca aaagcagcgc agaacaggat 360
agagaaaaca cgagagccac cctggaacag agactgaggg agagtgagga aagggccgca 420
gagctggcca gtcagctgga agcagccgca gccgcaaaga gcagcgcaga gcaggacagg 480
gaaaacacac gagcagccct ggaggaaaag ctgaggggat cagaggagag ggctgcagag 540
ctgggcaccc gagtcaaggc cagcagcgcc gcaaaggccc ttgccgagca ggaacgcgat 600
aggattaggg ctgctttgga agagaaactg agggatagcg aggccagagc tgccgaactg 660
accaccaagc tggaggccac tgtggccgcc aaatcaagtg ccgagcaaga gagagagaac 720
atcaaagtgg cagtcgaggc cactgagctg gagagagccc aggaagaggc tgaaaggctg 780
gcaggcgacc tggagaaagc tgaggaggag gcagaaagac tggcaggcga cctggaaaaa 840
gcccaagagg aagctgagac gctggctggc gtcaacgagc tggctgacaa ggacccagaa 900
ttggccgcct ttagggaaaa gcgcagggcc gctcacggag ccagagcaga cgaacccgag 960
ctggctgctg ccgacgggat tagcacacgc aatgccaggg ccggaagccg tggacgtcca 1020
gccgcacaga tcaatcccgc tgctgaagcc gtggatcccg tgactatcgc agctgagcca 1080
ctgtacgccg tgaccctcga cgaatacaag gccaaacaga ccgcactgga aaacgcagtt 1140
gaagtggcct gcgcagccga agagactgtg aaagagaaac tgagggagaa cagcgacctg 1200
atggtggagc tggaaaaggt gcgtgaccag gcttacgaga tggataggag gaggcaagaa 1260
gacggagccg caatggaagg ggagctgctg gttgtgctga tggagctcaa gaaactcaag 1320
ggaatcaacg acgccctgct ggctgtgctt agggacaaag agtgtgaggt gaaagagctt 1380
cgataccaca acgagttgtg ggttgaccca acgggagaca agaagcaggt ggtgacgagg 1440
cacactaaga tctttgacgg caactgggag aggattgtgc gagaacgacc cgaagggctg 1500
ttcgcagcct ttgtgatcga tagcagtaac gcctgccacg tccctgggga caacatcaaa 1560
caggtgtctt ttgaccacga cgtcgacatg gcactgcaga gggttcgtga agcagcagaa 1620
aaagcgaaat gcgaattaag cagtgcgatg gaaacagaag ttaatttacc atttattacc 1680
gctaacgcag atggcgcgca acatatccag atgcgcattt ctcgttctaa attcgaaggt 1740
atcacccaga ggttgattga tcgttcaatc gccccgtgta aacagtgtat gaaggatgca 1800
ggggttgagc tcaaagaaat taatgatgtt gtgcttgttg gcgggatgac aagaatgcca 1860
aaagttgttg aagaagtaaa aaagtttttt caaaaagatc cctttcgcgg cgtgaatccc 1920
gacgaggccg tcgctcttgg tgcggccacc ctgggcggag ttctgcgtgg tgatgtcaag 1980
ggtttagtgt tgctggatgt gacacctttg tcactgggaa ttgagactct gggtggtgtc 2040
tttactcgta tgataccgaa aaacactacc attcccacga aaaagtcgca gacctttttct 2100

-continued

```
actgctgccg acaatcagac acaggtcgga attaaggttt ttcaaggtga gcgtgaaatg   2160

gctgctgaca accagatgat ggggcagttc gacctggttg ggattccgcc cgcacctagg   2220

ggggtgcccc aaatcgaagt taccttcgac atagacgcca atggtatctg tcatgtcaca   2280

gcaaaagata aagcaacggg taaaacacag aatattacga tcacagcaaa cggaggattg   2340

agtaaagagc agattgaaca gatgattcgc gattcggaac aacatgctga ggccgatcgt   2400

gtcaagcgtg aactggtcga ggttagaaat aatgcggaga cccagcttac caccgcggaa   2460

cgtcaattag gtgaatggaa gtatgtttcc gatgcagaaa aggagaatgt aaaaacgctg   2520

gtcgccgagt tgcgtaaggc aatggaaaat ccaaatgttg cgaaagacga tctggctgca   2580

gcaacagaca aactacaaaa ggccgtaatg gaatgcggca gaaccgagta tcagcaagcc   2640

gccgctgcta acagcggctc tacgtcgaat agcggtgaac aacagcagca acaaggccag   2700

ggagaacaac agcaacagca gtctcaggga gaggaaacaa aactcgagca tcatcatcat   2760

catcat                                                              2766
```

<210> SEQ ID NO 4
<211> LENGTH: 922
<212> TYPE: PRT
<213> ORGANISM: Leishmania infantum

<400> SEQUENCE: 4

```
Met Ala Ser Met Thr Gly Gly Gln Gln Met Gly Arg Met Ile Glu Ala
1               5                   10                  15

Glu Glu Gln Ala Arg Arg Glu Ala Glu Glu Gln Ala Arg Arg Val Ala
            20                  25                  30

Glu Glu Gln Ala Arg Arg Glu Ala Glu Glu Gln Ala Arg Arg Glu Val
        35                  40                  45

Glu Leu Glu Glu Lys Leu Arg Gly Thr Glu Ala Arg Ala Ala Glu Leu
    50                  55                  60

Ala Ala Arg Leu Lys Ala Ile Ala Ala Met Lys Ala Ser Met Val Gln
65                  70                  75                  80

Glu Arg Glu Ser Ala Arg Asp Ala Leu Glu Glu Lys Leu Arg Gly Ser
                85                  90                  95

Glu Val Arg Ala Ala Glu Leu Ala Ala Arg Leu Lys Ala Ala Val Ala
            100                 105                 110

Ala Lys Ser Ser Ala Glu Gln Asp Arg Glu Asn Thr Arg Ala Thr Leu
        115                 120                 125

Glu Gln Arg Leu Arg Glu Ser Glu Glu Arg Ala Ala Glu Leu Ala Ser
    130                 135                 140

Gln Leu Glu Ala Ala Ala Ala Ala Lys Ser Ser Ala Glu Gln Asp Arg
145                 150                 155                 160

Glu Asn Thr Arg Ala Ala Leu Glu Glu Lys Leu Arg Gly Ser Glu Glu
                165                 170                 175

Arg Ala Ala Glu Leu Gly Thr Arg Val Lys Ala Ser Ser Ala Ala Lys
            180                 185                 190

Ala Leu Ala Glu Gln Glu Arg Asp Arg Ile Arg Ala Ala Leu Glu Glu
        195                 200                 205

Lys Leu Arg Asp Ser Glu Ala Arg Ala Ala Glu Leu Thr Thr Lys Leu
    210                 215                 220

Glu Ala Thr Val Ala Ala Lys Ser Ser Ala Glu Gln Glu Arg Glu Asn
225                 230                 235                 240

Ile Lys Val Ala Val Glu Ala Thr Glu Leu Glu Arg Ala Gln Glu Glu
                245                 250                 255
```

-continued

```
Ala Glu Arg Leu Ala Gly Asp Leu Glu Lys Ala Glu Glu Glu Ala Glu
            260                 265                 270

Arg Leu Ala Gly Asp Leu Glu Lys Ala Gln Glu Glu Ala Glu Thr Leu
        275                 280                 285

Ala Gly Val Asn Glu Leu Ala Asp Lys Asp Pro Glu Leu Ala Ala Phe
    290                 295                 300

Arg Glu Lys Arg Arg Ala Ala His Gly Ala Arg Ala Asp Glu Pro Glu
305                 310                 315                 320

Leu Ala Ala Ala Asp Gly Ile Ser Thr Arg Asn Ala Arg Ala Gly Ser
                325                 330                 335

Arg Gly Arg Pro Ala Ala Gln Ile Asn Pro Ala Ala Glu Ala Val Asp
            340                 345                 350

Pro Val Thr Ile Ala Ala Glu Pro Leu Tyr Ala Val Thr Leu Asp Glu
        355                 360                 365

Tyr Lys Ala Lys Gln Thr Ala Leu Glu Asn Ala Val Glu Val Ala Cys
    370                 375                 380

Ala Ala Glu Glu Thr Val Lys Glu Lys Leu Arg Glu Asn Ser Asp Leu
385                 390                 395                 400

Met Val Glu Leu Glu Lys Val Arg Asp Gln Ala Tyr Glu Met Asp Arg
                405                 410                 415

Arg Arg Gln Glu Asp Gly Ala Ala Met Glu Gly Glu Leu Leu Val Val
            420                 425                 430

Leu Met Glu Leu Lys Lys Leu Lys Gly Ile Asn Asp Ala Leu Leu Ala
        435                 440                 445

Val Leu Arg Asp Lys Glu Cys Glu Val Lys Glu Leu Arg Tyr His Asn
    450                 455                 460

Glu Leu Trp Val Asp Pro Thr Gly Asp Lys Lys Gln Val Val Thr Arg
465                 470                 475                 480

His Thr Lys Ile Phe Asp Gly Asn Trp Glu Arg Ile Val Arg Glu Arg
                485                 490                 495

Pro Glu Gly Leu Phe Ala Ala Phe Val Ile Asp Ser Ser Asn Ala Cys
            500                 505                 510

His Val Pro Gly Asp Asn Ile Lys Gln Val Ser Phe Asp His Asp Val
        515                 520                 525

Asp Met Ala Leu Gln Arg Val Arg Glu Ala Ala Glu Lys Ala Lys Cys
    530                 535                 540

Glu Leu Ser Ser Ala Met Glu Thr Glu Val Asn Leu Pro Phe Ile Thr
545                 550                 555                 560

Ala Asn Ala Asp Gly Ala Gln His Ile Gln Met Arg Ile Ser Arg Ser
                565                 570                 575

Lys Phe Glu Gly Ile Thr Gln Arg Leu Ile Asp Arg Ser Ile Ala Pro
            580                 585                 590

Cys Lys Gln Cys Met Lys Asp Ala Gly Val Glu Leu Lys Glu Ile Asn
        595                 600                 605

Asp Val Val Leu Val Gly Gly Met Thr Arg Met Pro Lys Val Val Glu
    610                 615                 620

Glu Val Lys Lys Phe Phe Gln Lys Asp Pro Phe Arg Gly Val Asn Pro
625                 630                 635                 640

Asp Glu Ala Val Ala Leu Gly Ala Ala Thr Leu Gly Gly Val Leu Arg
                645                 650                 655

Gly Asp Val Lys Gly Leu Val Leu Leu Asp Val Thr Pro Leu Ser Leu
            660                 665                 670
```

-continued

```
Gly Ile Glu Thr Leu Gly Gly Val Phe Thr Arg Met Ile Pro Lys Asn
        675                 680                 685

Thr Thr Ile Pro Thr Lys Lys Ser Gln Thr Phe Ser Thr Ala Ala Asp
    690                 695                 700

Asn Gln Thr Gln Val Gly Ile Lys Val Phe Gln Gly Glu Arg Glu Met
705                 710                 715                 720

Ala Ala Asp Asn Gln Met Met Gly Gln Phe Asp Leu Val Gly Ile Pro
                725                 730                 735

Pro Ala Pro Arg Gly Val Pro Gln Ile Glu Val Thr Phe Asp Ile Asp
            740                 745                 750

Ala Asn Gly Ile Cys His Val Thr Ala Lys Asp Lys Ala Thr Gly Lys
        755                 760                 765

Thr Gln Asn Ile Thr Ile Thr Ala Asn Gly Gly Leu Ser Lys Glu Gln
    770                 775                 780

Ile Glu Gln Met Ile Arg Asp Ser Glu Gln His Ala Glu Ala Asp Arg
785                 790                 795                 800

Val Lys Arg Glu Leu Val Glu Val Arg Asn Asn Ala Glu Thr Gln Leu
                805                 810                 815

Thr Thr Ala Glu Arg Gln Leu Gly Glu Trp Lys Tyr Val Ser Asp Ala
            820                 825                 830

Glu Lys Glu Asn Val Lys Thr Leu Val Ala Glu Leu Arg Lys Ala Met
        835                 840                 845

Glu Asn Pro Asn Val Ala Lys Asp Asp Leu Ala Ala Ala Thr Asp Lys
    850                 855                 860

Leu Gln Lys Ala Val Met Glu Cys Gly Arg Thr Glu Tyr Gln Gln Ala
865                 870                 875                 880

Ala Ala Ala Asn Ser Gly Ser Thr Ser Asn Ser Gly Glu Gln Gln Gln
                885                 890                 895

Gln Gln Gly Gln Gly Glu Gln Gln Gln Gln Gln Ser Gln Gly Glu Glu
            900                 905                 910

Thr Lys Leu Glu His His His His His His
        915                 920
```

```
<210> SEQ ID NO 5
<211> LENGTH: 1656
<212> TYPE: DNA
<213> ORGANISM: Leishmania infantum

<400> SEQUENCE: 5

atggcaaaaa aactgctgtt cgcgattccg ctggtggtgc cgttctatag ccataccatg      60

gctagcatga ctggtggaca gcaaatgggt cggatgatcg aggccgagga acaggccagg     120

agggaggctg aagagcaggc cagacgcgtc gccgaggaac aggccaggag ggaggcagag     180

gagcaagcca ggagagaggt cgagcttgaa gagaaactga ggggaactga agccagagct     240

gccgaactcg ccgccaggct gaaggccatt gctgccatga aagcaagcat ggtgcaggaa     300

agggagtccg cacgcgacgc actggaagaa aagctgaggg gcagcgaggt gagggccgca     360

gagctcgcag ccagactcaa agccgcagtg gcagccaaaa gcagcgcaga acaggataga     420

gaaaacacga gagccaccct ggaacagaga ctgagggaga gtgaggaaag ggccgcagag     480

ctggccagtc agctggaagc agccgcagcc gcaaagagca gcgcagagca ggacagggaa     540

aacacacgag cagccctgga ggaaaagctg aggggatcag aggagagggc tgcagagctg     600

ggcacccgag tcaaggccag cagcgccgca aaggcccttg ccgagcagga acgcgatagg     660

attagggctg ctttggaaga gaaactgagg gatagcgagg ccagagctgc cgaactgacc     720
```

-continued

```
accaagctgg aggccactgt ggccgccaaa tcaagtgccg agcaagagag agagaacatc    780

aaagtggcag tcgaggccac tgagctggag agagcccagg aagaggctga aaggctggca    840

ggcgacctgg agaaagctga ggaggaggca gaaagactgg caggcgacct ggaaaaagcc    900

caagaggaag ctgagacgct ggctggcgtc aacgagctgg ctgacaagga cccagaattg    960

gccgccttta gggaaaagcg cagggccgct cacggagcca gagcagacga acccgagctg   1020

gctgctgccg acgggattag cacacgcaat gccagggccg gaagccgtgg acgtccagcc   1080

gcacagatca atcccgctgc tgaagccgtg gatcccgtga ctatcgcagc tgagccactg   1140

tacgccgtga ccctcgacga atacaaggcc aaacagaccg cactggaaaa cgcagttgaa   1200

gtggcctgcg cagccgaaga gactgtgaaa gagaaactga gggagaacag cgacctgatg   1260

gtggagctgg aaaaggtgcg tgaccaggct tacgagatgg ataggaggag gcaagaagac   1320

ggagccgcaa tggaagggga gctgctggtt gtgctgatgg agctcaagaa actcaaggga   1380

atcaacgacg ccctgctggc tgtgcttagg gacaaagagt gtgaggtgaa agagcttcga   1440

taccacaacg agttgtgggt tgacccaacg ggagacaaga agcaggtggt gacgaggcac   1500

actaagatct ttgacggcaa ctgggagagg attgtgcgag aacgacccga agggctgttc   1560

gcagcctttg tgatcgatag cagtaacgcc tgccacgtcc ctggggacaa catcaaacag   1620

gtgtcttttg accacgacca tcatcatcat catcat                             1656
```

<210> SEQ ID NO 6
<211> LENGTH: 552
<212> TYPE: PRT
<213> ORGANISM: Leishmania infantum

<400> SEQUENCE: 6

```
Met Ala Lys Lys Leu Leu Phe Ala Ile Pro Leu Val Val Pro Phe Tyr
1               5                   10                  15

Ser His Thr Met Ala Ser Met Thr Gly Gly Gln Gln Met Gly Arg Met
            20                  25                  30

Ile Glu Ala Glu Glu Gln Ala Arg Arg Glu Ala Glu Glu Gln Ala Arg
        35                  40                  45

Arg Val Ala Glu Glu Gln Ala Arg Arg Glu Ala Glu Glu Gln Ala Arg
    50                  55                  60

Arg Glu Val Glu Leu Glu Glu Lys Leu Arg Gly Thr Glu Ala Arg Ala
65                  70                  75                  80

Ala Glu Leu Ala Ala Arg Leu Lys Ala Ile Ala Ala Met Lys Ala Ser
                85                  90                  95

Met Val Gln Glu Arg Glu Ser Ala Arg Asp Ala Leu Glu Glu Lys Leu
            100                 105                 110

Arg Gly Ser Glu Val Arg Ala Ala Glu Leu Ala Ala Arg Leu Lys Ala
        115                 120                 125

Ala Val Ala Ala Lys Ser Ser Ala Glu Gln Asp Arg Glu Asn Thr Arg
    130                 135                 140

Ala Thr Leu Glu Gln Arg Leu Arg Glu Ser Glu Glu Arg Ala Ala Glu
145                 150                 155                 160

Leu Ala Ser Gln Leu Glu Ala Ala Ala Ala Ala Lys Ser Ser Ala Glu
                165                 170                 175

Gln Asp Arg Glu Asn Thr Arg Ala Ala Leu Glu Glu Lys Leu Arg Gly
            180                 185                 190

Ser Glu Glu Arg Ala Ala Glu Leu Gly Thr Arg Val Lys Ala Ser Ser
        195                 200                 205
```

-continued

```
Ala Ala Lys Ala Leu Ala Glu Gln Glu Arg Asp Arg Ile Arg Ala Ala
    210                 215                 220

Leu Glu Glu Lys Leu Arg Asp Ser Glu Ala Arg Ala Ala Glu Leu Thr
225                 230                 235                 240

Thr Lys Leu Glu Ala Thr Val Ala Ala Lys Ser Ser Ala Glu Gln Glu
                245                 250                 255

Arg Glu Asn Ile Lys Val Ala Val Glu Ala Thr Glu Leu Glu Arg Ala
            260                 265                 270

Gln Glu Glu Ala Glu Arg Leu Ala Gly Asp Leu Glu Lys Ala Glu Glu
        275                 280                 285

Glu Ala Glu Arg Leu Ala Gly Asp Leu Glu Lys Ala Gln Glu Glu Ala
    290                 295                 300

Glu Thr Leu Ala Gly Val Asn Glu Leu Ala Asp Lys Asp Pro Glu Leu
305                 310                 315                 320

Ala Ala Phe Arg Glu Lys Arg Arg Ala Ala His Gly Ala Arg Ala Asp
                325                 330                 335

Glu Pro Glu Leu Ala Ala Ala Asp Gly Ile Ser Thr Arg Asn Ala Arg
            340                 345                 350

Ala Gly Ser Arg Gly Arg Pro Ala Ala Gln Ile Asn Pro Ala Ala Glu
        355                 360                 365

Ala Val Asp Pro Val Thr Ile Ala Ala Glu Pro Leu Tyr Ala Val Thr
    370                 375                 380

Leu Asp Glu Tyr Lys Ala Lys Gln Thr Ala Leu Glu Asn Ala Val Glu
385                 390                 395                 400

Val Ala Cys Ala Ala Glu Glu Thr Val Lys Glu Lys Leu Arg Glu Asn
                405                 410                 415

Ser Asp Leu Met Val Glu Leu Glu Lys Val Arg Asp Gln Ala Tyr Glu
            420                 425                 430

Met Asp Arg Arg Arg Gln Glu Asp Gly Ala Ala Met Glu Gly Glu Leu
        435                 440                 445

Leu Val Val Leu Met Glu Leu Lys Lys Leu Lys Gly Ile Asn Asp Ala
    450                 455                 460

Leu Leu Ala Val Leu Arg Asp Lys Glu Cys Glu Val Lys Glu Leu Arg
465                 470                 475                 480

Tyr His Asn Glu Leu Trp Val Asp Pro Thr Gly Asp Lys Lys Gln Val
                485                 490                 495

Val Thr Arg His Thr Lys Ile Phe Asp Gly Asn Trp Glu Arg Ile Val
            500                 505                 510

Arg Glu Arg Pro Glu Gly Leu Phe Ala Ala Phe Val Ile Asp Ser Ser
        515                 520                 525

Asn Ala Cys His Val Pro Gly Asp Asn Ile Lys Gln Val Ser Phe Asp
    530                 535                 540

His Asp His His His His His His
545                 550
```

<210> SEQ ID NO 7
<211> LENGTH: 1956
<212> TYPE: DNA
<213> ORGANISM: Leishmania infantum

<400> SEQUENCE: 7

```
atggcaaaaa aactgctgtt cgcgattccg ctggtggtgc cgttctatag ccataccatg      60

gctagcatga ctggtggaca gcaaatgggt cggatgatcg aggccgagga acaggccagg     120
```

-continued

```
agggaggctg aagagcaggc cagacgcgtc gccgaggaac aggccaggag ggaggcagag    180
gagcaagcca ggagagaggt cgagcttgaa gagaaactga ggggaactga agccagagct    240
gccgaactcg ccgccaggct gaaggccatt gctgccatga aagcaagcat ggtgcaggaa    300
agggagtccg cacgcgacgc actggaagaa aagctgaggg gcagcgaggt gagggccgca    360
gagctcgcag ccagactcaa agccgcagtg gcagccaaaa gcagcgcaga acaggataga    420
gaaaacacga gagccaccct ggaacagaga ctgagggaga gtgaggaaag ggccgcagag    480
ctggccagtc agctggaagc agccgcagcc gcaaagagca gcgcagagca ggacagggaa    540
aacacacgag cagccctgga ggaaaagctg aggggatcag aggagagggc tgcagagctg    600
ggcacccgag tcaaggccag cagcgccgca aaggcccttg ccgagcagga acgcgatagg    660
attagggctg ctttggaaga gaaactgagg gatagcgagg ccagagctgc cgaactgacc    720
accaagctgg aggccactgt ggccgccaaa tcaagtgccg agcaagagag agagaacatc    780
aaagtggcag tcgaggtcga cgagctgcag aaagcccagg aggacggcga acgtcaaaag    840
gcagacaata gacagctggc ctcagacaac gagagactgg ccaccgagct ggaaagagct    900
caggaggaag cagagcgcct ggccggagac ctggagaaag cagaagaaga ggctgagcga    960
cttgcaggcg acctggagaa ggcccaggaa gaggcagaaa cactggctgg ggagctccaa   1020
aaggcccagg aggacgggga acgtcaaaag gcagacaatc ggcagctggc ctcagacaac   1080
gaaaggctgc tcgaggccac tgagctggag agagcccagg aagaggctga aaggctggca   1140
ggcgacctgg agaaagctga ggaggaggca gaaagactgg caggcgacct ggaaaaagcc   1200
caagaggaag ctgagacgct ggctggcgtg gacgagctgg ctgacaagga cccagaattg   1260
gccgccttta gggaaaagcg cagggccgct cacggagcca gagcagacga acccgagctg   1320
gctgctgccg acgggattag cacacgcaat gccagggccg gaagccgtgg acgtccagcc   1380
gcacagatca atcccgctgc tgaagccgtg gatcccgtga ctatcgcagc tgagccactg   1440
tacgccgtga ccctcgacga atacaaggcc aaacagaccg cactggaaaa cgcagttgaa   1500
gtggcctgcg cagccgaaga gactgtgaaa gagaaactga gggagaacag cgacctgatg   1560
gtggagctgg aaaaggtgcg tgaccaggct tacgagatgg ataggaggag gcaagaagac   1620
ggagccgcga tggaagggga gctgctggtt gtgctgatgg agctcaagaa actcaaggga   1680
atcaacgacg ccctgctggc tgtgcttagg gacaaagagt gtgaggtgaa agagcttcga   1740
taccacaacg agttgtgggt tgacccaacg ggagacaaga agcaggtggt gacgaggcac   1800
actaagatct ttgacggcaa ttgggagagg attgtgcgag aacgacccga agggctgttc   1860
gcagcctttg tgatcgatag cagtaacgcc tgccacgtcc ctggggacaa catcaaacag   1920
gtgtcttttg accacgacca tcatcatcat catcat                             1956
```

<210> SEQ ID NO 8
<211> LENGTH: 652
<212> TYPE: PRT
<213> ORGANISM: Leishmania infantum

<400> SEQUENCE: 8

```
Met Ala Lys Lys Leu Leu Phe Ala Ile Pro Leu Val Val Pro Phe Tyr
1               5                   10                  15

Ser His Thr Met Ala Ser Met Thr Gly Gly Gln Gln Met Gly Arg Met
            20                  25                  30

Ile Glu Ala Glu Glu Gln Ala Arg Arg Glu Ala Glu Glu Gln Ala Arg
        35                  40                  45
```

-continued

```
Arg Val Ala Glu Glu Gln Ala Arg Arg Glu Ala Glu Glu Gln Ala Arg
    50                  55                  60

Arg Glu Val Glu Leu Glu Glu Lys Leu Arg Gly Thr Glu Ala Arg Ala
65                  70                  75                  80

Ala Glu Leu Ala Ala Arg Leu Lys Ala Ile Ala Ala Met Lys Ala Ser
                85                  90                  95

Met Val Gln Glu Arg Glu Ser Ala Arg Asp Ala Leu Glu Glu Lys Leu
            100                 105                 110

Arg Gly Ser Glu Val Arg Ala Ala Glu Leu Ala Ala Arg Leu Lys Ala
        115                 120                 125

Ala Val Ala Ala Lys Ser Ser Ala Glu Gln Asp Arg Glu Asn Thr Arg
    130                 135                 140

Ala Thr Leu Glu Gln Arg Leu Arg Glu Ser Glu Glu Arg Ala Ala Glu
145                 150                 155                 160

Leu Ala Ser Gln Leu Glu Ala Ala Ala Ala Ala Lys Ser Ser Ala Glu
                165                 170                 175

Gln Asp Arg Glu Asn Thr Arg Ala Ala Leu Glu Glu Lys Leu Arg Gly
            180                 185                 190

Ser Glu Glu Arg Ala Ala Glu Leu Gly Thr Arg Val Lys Ala Ser Ser
        195                 200                 205

Ala Ala Lys Ala Leu Ala Glu Gln Glu Arg Asp Arg Ile Arg Ala Ala
    210                 215                 220

Leu Glu Glu Lys Leu Arg Asp Ser Glu Ala Arg Ala Ala Glu Leu Thr
225                 230                 235                 240

Thr Lys Leu Glu Ala Thr Val Ala Ala Lys Ser Ser Ala Glu Gln Glu
                245                 250                 255

Arg Glu Asn Ile Lys Val Ala Val Glu Val Asp Glu Leu Gln Lys Ala
            260                 265                 270

Gln Glu Asp Gly Glu Arg Gln Lys Ala Asp Asn Arg Gln Leu Ala Ser
        275                 280                 285

Asp Asn Glu Arg Leu Ala Thr Glu Leu Glu Arg Ala Gln Glu Glu Ala
    290                 295                 300

Glu Arg Leu Ala Gly Asp Leu Glu Lys Ala Glu Glu Glu Ala Glu Arg
305                 310                 315                 320

Leu Ala Gly Asp Leu Glu Lys Ala Gln Glu Glu Ala Glu Thr Leu Ala
                325                 330                 335

Gly Glu Leu Gln Lys Ala Gln Glu Asp Gly Glu Arg Gln Lys Ala Asp
            340                 345                 350

Asn Arg Gln Leu Ala Ser Asp Asn Glu Arg Leu Leu Glu Ala Thr Glu
        355                 360                 365

Leu Glu Arg Ala Gln Glu Glu Ala Glu Arg Leu Ala Gly Asp Leu Glu
    370                 375                 380

Lys Ala Glu Glu Glu Ala Glu Arg Leu Ala Gly Asp Leu Glu Lys Ala
385                 390                 395                 400

Gln Glu Glu Ala Glu Thr Leu Ala Gly Val Asp Glu Leu Ala Asp Lys
                405                 410                 415

Asp Pro Glu Leu Ala Ala Phe Arg Glu Lys Arg Arg Ala Ala His Gly
            420                 425                 430

Ala Arg Ala Asp Glu Pro Glu Leu Ala Ala Ala Asp Gly Ile Ser Thr
        435                 440                 445

Arg Asn Ala Arg Ala Gly Ser Arg Gly Arg Pro Ala Ala Gln Ile Asn
    450                 455                 460

Pro Ala Ala Glu Ala Val Asp Pro Val Thr Ile Ala Ala Glu Pro Leu
```

-continued

```
465                 470                 475                 480

Tyr Ala Val Thr Leu Asp Glu Tyr Lys Ala Lys Gln Thr Ala Leu Glu
                485                 490                 495

Asn Ala Val Glu Val Ala Cys Ala Ala Glu Glu Thr Val Lys Glu Lys
            500                 505                 510

Leu Arg Glu Asn Ser Asp Leu Met Val Glu Leu Glu Lys Val Arg Asp
        515                 520                 525

Gln Ala Tyr Glu Met Asp Arg Arg Arg Gln Glu Asp Gly Ala Ala Met
    530                 535                 540

Glu Gly Glu Leu Leu Val Val Leu Met Glu Leu Lys Lys Leu Lys Gly
545                 550                 555                 560

Ile Asn Asp Ala Leu Leu Ala Val Leu Arg Asp Lys Glu Cys Glu Val
                565                 570                 575

Lys Glu Leu Arg Tyr His Asn Glu Leu Trp Val Asp Pro Thr Gly Asp
            580                 585                 590

Lys Lys Gln Val Val Thr Arg His Thr Lys Ile Phe Asp Gly Asn Trp
        595                 600                 605

Glu Arg Ile Val Arg Glu Arg Pro Glu Gly Leu Phe Ala Ala Phe Val
    610                 615                 620

Ile Asp Ser Ser Asn Ala Cys His Val Pro Gly Asp Asn Ile Lys Gln
625                 630                 635                 640

Val Ser Phe Asp His Asp His His His His His His
                645                 650
```

CHIMERIC PROTEIN, METHOD OF PRODUCTION AND USE THEREOF, AND ALSO A NUCLEIC ACID MOLECULE, EXPRESSION CASSETTE, EXPRESSION VECTOR, HOST CELL, COMPOSITION FOR THE DIAGNOSIS OF LEISHMANIASIS, KIT FOR THE DIAGNOSIS OF LEISHMANIASIS AND METHOD OF DIAGNOSIS OF LEISHMANIASIS IN VITRO

This application is a national stage application under 35 U.S.C. 371 of International Application No. PCT/BR2020/050044, filed Feb. 14, 2020, which claims the benefit of Brazilian Patent Application No. BR1020190036397, filed Feb. 22, 2019, the disclosure of which is explicitly incorporated herein in its entirety by reference.

FIELD OF INVENTION

The present invention relates to the field of diagnostic medicine and biotechnology. Specifically, the present invention relates to polypeptides, more specifically chimeric proteins, for the diagnostic application of *Leishmania infantum* in humans, dogs and other vertebrate hosts.

GROUNDS FOR THE INVENTION

Leishmaniasis is an infectious-parasitic disease caused by flagellated protozoa belonging to the family Trypanosomatidae and the genus *Leishmania.*

These protozoa have a heteroxenous life cycle, living alternately in vertebrate hosts (including man and other wild and/or domestic mammals such as dogs) and vector dipterous insects, the latter belonging to the genera *Phlebotomus* and *Lutzomyia* (PACE, 2014).

Currently, there are about 30 known species of *Leishmania*, of which 10 are present in the Old World and the other 20 in the New World, with about 20 of them being capable of causing cutaneous and/or Visceral Leishmaniasis.

The protozoa of the genus *Leishmania* have two very distinct evolutionary forms, both functionally and morphologically, the promastigotes and the amastigotes.

The amastigote forms are present in the vertebrate host, presenting a spheroid to ovoid shape. They are immobile, obligatory intracellular forms, as they have a short flagellum situated within the flagellar pouch, which functions primarily as a site for endocytosis and exocytosis. They develop in vacuoles of cells of the mononuclear phagocytic system and, consequently, they are acidophilic cells, adapted to the low pH of such environment. The promastigote forms are found in the intestine of the vector (invertebrate host) and are elongated with variation in length. They are extracellular, flagellate forms, which can present as procyclic promastigotes, defined as more ovoid, mobile and replicative cells, or as metacyclic promastigotes, infective forms, more elongated and with no capacity for proliferation. (KAYE; SCOTT, 2011; MURRAY et al., 2005).

Leishmaniasis has as vectors, invertebrates belonging to the phylum Arthropoda, class Insecta, order Diptera, family Psychodidae, subfamily Phlebotominae. Two genera are known, *Phlebotomus* (present in the Old World) and *Lutzomyia* (present in the New World) (AKHOUNDI et al., 2016; READY, 2013).

The life cycle of the *Leishmania* parasite is divided into two stages, the first in the vertebrate host (mammal) and the second in the invertebrate host (sand fly). This cycle begins when the female infected sand fly mosquito ingests blood from the vertebrate host (dog or human). While ingesting the blood, the insect regurgitates the metacyclic promastigotes of the parasite (infective form, located in the stomatal valve of the vector) together with its salivary components.

The metacyclic promastigotes are then phagocytized by different types of immune system cells found at the site of inoculation where they differentiate into the amastigote forms. This cycle is completed when macrophages infected by amastigotes are ingested by another sand fly, where they will go through various stages of development until they return to the metacyclic form. Each of these stages is characterized by morphological and functional changes in order to ensure survival within the vector.

After the differentiation steps, the metacyclic promastigotes will migrate to the stomatal valve to be inoculated into another vertebrate host and continue the cycle (KAMHAWI, 2006; KAYE; SCOTT, 2011).

Leishmaniasis is considered as the main neglected disease, mainly affecting individuals from developing countries. Prevalence occurs in tropical and subtropical regions of Africa, Asia, the Mediterranean, Southwestern Europe, and South and Central America. This disease is endemic in 98 countries, of which 72 are developing countries, with more than one million new cases registered annually (ALVAR et al., 2012).

This disease can be classified into two main forms, which vary according to symptoms and clinical form and are associated with different *Leishmania* species. Cutaneous Leishmaniasis (LC) is characterized by lesions on the skin that can spread to the mucous membranes, while in Visceral Leishmaniasis (LV) the parasite lodges in internal organs such as the spleen, lymph nodes, bone marrow, and liver. VL, caused by *L. donovani* and *L. infantum*, has a lower incidence than LC, but is a more severe and fatal form, if untreated (CHAPPUIS et al., 2007).

The domestic dog plays a major role in the epidemiology of VL in endemic areas, as it is the main domestic reservoir of the disease. This importance comes from the fact that Calazar (the popular name given to the disease) is more prevalent in the canine population than in the human, and human cases are usually preceded by canine cases. (QUINNELL; COURTENAY, 2009).

The immunology and pathogenesis of Leishmaniasis are complex and are associated with a large number of genetic and cellular factors that implicate host resistance and susceptibility. For some time now, it has been known that the control of infection by the parasite seems to depend on an immune response associated with CD4+ T lymphocytes associated with Th1 response and interleukins (IL) IL-12, IL-18, IL-27 that activate macrophages. Since IL-12, IFN-? also generates an effective response by increasing the production of the Th1 response.

On the other hand, the Th2 response, associated with cytokines such as IL-10 and IL-4, sustains the persistence of the parasite, so the development of VL infection will then depend on the response developed by the vertebrate host. If there is an increase in the Th2 response compared to the Th1 response, the deactivation of macrophages leads to the host's failure to control the infection.

More recently it has been observed that other types of immune system cells, such as those called Th17, also seem to play a critical role in defining how the vertebrate host reacts to infection with the causative agent of Leishmaniasis (SRIVASTAVA et al., 2016).

Knowledge about the immune response to Leishmaniasis has been enhanced with the use of experimental models, such as the mouse, and studies with human cells, but little is known about how it occurs in dogs.

The clinical symptoms of VL are associated with a systemic infection and include prolonged persistent fever, loss of appetite, weight loss, fatigue, cough, abdominal pain, edema and diarrhea, as well as enlargement of the spleen, liver and lymph nodes, pancytopenia, anemia and hypergammaglobulinemia.

In their early stages, these symptoms can easily be confused with those of other diseases leading to a delay in the diagnosis of the disease and complicating its treatment (SINGH; SUNDAR, 2015; SRIVASTAVA et al., 2011; SRIVIDYA et al., 2012).

The canine VL diagnosis is also an extremely relevant point for the control of the disease as a whole, since clinically healthy dogs can be infected and even in cases where some clinical symptoms are apparent these can lead to an erroneous identification of the pathology (GOMES et al., 2008; NOLI; SARIDOMICHELAKIS, 2014).

In dogs, VL has slow evolution and insidious onset, being a systemic and severe disease, whose clinical manifestations are dependent on the type of immune response expressed by the infected animal.

The clinical picture of infected dogs presents a spectrum of clinical features ranging from the apparent healthy state to a severe end-stage. Initially, the parasites are present at the site of the bite, but later infection of viscera and dispersal through the dermis occurs. Hair loss caused by infection exposes large areas of extensively parasitized skin (PALTRINIERI et al., 2016; SARIDOMICHELAKIS, 2009).

The gold standard for confirming the diagnosis of VL in both humans and dogs is the identification of the *Leishmania* parasite in material taken by biopsy of internal organs, such as the bone marrow and spleen. This method, however, is insensitive, labor-intensive, and requires invasive procedures (CHAPPUIS et al., 2007; SRIVASTAVA et al., 2011; SUNDAR; RAI, 2002).

Molecular tests have more recently been developed based on variations on the PCR technique and, although they may show variable results for sensitivity and specificity according to the method used, in general they are quite satisfactory with minimal invasiveness, but all require equipment that is not suitable for field use (DE RUITER et al., 2014).

VL, however, is characterized by hypergammaglobulinemia or high production of anti-*Leishmania* antibodies, which facilitates the use of immunological techniques to detect these antibodies. Among these techniques, the following stand out: IIF (indirect immunofluorescence), DAT (direct agglutination test) immunoblotting (Western-Blot) ELISA (enzyme immunoassay) and rapid test.

IIF has considerable sensitivity, but low specificity, where cross-reactions are observed at low titers with other diseases such as Chagas disease, Malaria and Schistosomiasis. Its application requires a high level of skill, experience and also specialized, high-cost equipment. In addition, the serial dilutions of serum make the test laborious for screenings with large numbers of samples, and it is also a reaction not well suited for large-scale epidemiological studies.

DAT is based on the detection of direct agglutination of *Leishmania* promastigotes that react with anti-*Leishmania* antibodies in serum, resulting in the agglutination of the promastigotes, and makes up an easy technique to perform. However, there are difficulties in the standardization and quality control of the antigen.

One of the limitations of DAT is the long incubation time required (18 hours) and the many dilutions that must be made for serum or plasma, which make the test laborious and not suitable for screening large numbers of samples.

The ELISA test is a modern methodology that allows a large number of tests to be performed in a short period of time, and is the most widely used for VL immunodiagnostic. This test has high sensitivity and allows the detection of low antibody titers, but may be inaccurate in detecting subclinical or asymptomatic cases, because the performance of the ELISA test in the diagnosis of VL, especially canine VL, is related not only to the type of antigen used, but also to the clinical status of the dog being tested.

A rapid alternative to ELISA and using minimal infrastructure is the rapid immunochromatographic test, which is based on nitrocellulose membrane immunochromatography, where a recombinant antigen is used (rK39), fixed on paper (BOELAERT et al., 2004; CAÑAVATE et al., 2011; CHAPPUIS et al., 2007; METTLER et al., 2005; SRIVASTAVA et al., 2011; SUNDAR; RAI, 2002).

The recombinant rK39 antigen is a 39 amino-acid peptide from *L. infantum* that has been identified as highly attractive for the human VL diagnosis (SINGH et al., 1995). The rK39-based rapid test showed high sensitivity and specificity in human VL recognition tests (SUNDAR et al., 1998).

Thus, this test came to be seen as a promising tool in VL control programs, since it requires a small amount of peripheral blood and is quick to perform and read (between 10 and 20 minutes) and can be used in field conditions (CHAPPUIS et al., 2006, 2007; GOMES et al., 2008).

However, discrepancies have been raised between papers that have used rK39 in different countries around the world, for example on the African continent, and have shown markedly different results. These data suggest that the sensitivity of an antigen may vary with respect to the region in which it is being used (BOELAERT et al., 2014; SRIVASTAVA et al., 2011).

In Brazil, the K39 diagnostic performance was considered only reasonable for the confirmation of infection in suspected cases of canine VL (QUINNELL et al., 2013). Recently, another immunochromatographic rapid test has been used in Brazil based on the recombinant rK28 antigen, a synthetic gene generated from the fusion of several repeat sequences of *L. donovani* haspb 1 and rK39, with ELISA as the confirmatory method (PATTABHI et al., 2010).

The test was performed with serum from dogs infected with the disease from three states (Bahia, Rio Grande do Norte and Minas Gerais) and showed high sensitivity in symptomatic dogs, but lower sensitivity in asymptomatic dogs (FRAGA et al., 2016).

In previous work carried out by some of the authors of the present invention, and directly linked to the present invention, an attempt was made to identify new polypeptides of *L. infantum* with potential for use in the VL serological diagnosis (Oliveira et al., 2011; Magalhaes et al., 2017).

New antigens were then identified by screening *L. infantum* cDNA expression libraries with sera from animals and human patients affected by this disease. As a result of this screening, and after sequence homology analysis of the clones obtained with sequences from *L. infantum* and *L. major* genomic databases, clones encoding five distinct proteins, designated Lci1 to Lci5, were identified.

Fragments of these were then expressed in *Escherichia coli* and the derived recombinant proteins were then evaluated for their potential in VL diagnosis using ELISA assays with sera from animals and humans affected by this disease.

An important result derived from these analyzes is that the most efficient antigens for detecting human VL were not the best ones for canine VL and vice versa. (OLIVEIRA et al., 2011).

Two of the generated recombinant proteins (Lci1A and Lci2B) were then evaluated in a rapid immunochromatographic test for the diagnosis of dogs infected with *L. infantum*, it was possible to verify that these two antigens in partnership with the test based on the rK28 protein increased the sensitivity from 88% to 93.5%, showing that the combination of antigens is an excellent alternative in VL diagnosis (FRAGA et al., 2014).

Magalhães et al., (2017) subsequently identified a second set of novel *L. infantum* antigens in a new expression library screening, this time using a genomic library and a set of sera from patients infected with this pathogen. Seven new antigens (Lci6 to Lci12) were identified, of which five have not yet been properly characterized in *Leishmania.*

Fragments of six of these were expressed in *Escherichia coli* and the respective recombinant proteins evaluated also for their potential in human and canine VL diagnosis. None of these was considered satisfactory for the human VL diagnosis (MAGALHÃES et al., 2017).

Magalhães et al. further evaluated one more protein identified in an earlier screening of *L. infantum* cDNA library performed independently (CAMPOS et al., 2008) and then named Lci13, confirming that this protein was not considered satisfactory for the human VL diagnosis.

Patent application PI 0900961-2 relates to 13 different *Leishmania* antigens (Lci1 to Lci13) for use in the leishmaniasis diagnosis. However, as none of the new identified antigens proved to be efficient for the diagnosis of both human and canine forms of VL and with the finding that the available serological tests were not efficient enough for the diagnosis of canine VL, we sought to then alternatives for the development of a unique system for the diagnosis of VL in humans and dogs.

Furthermore, a simple diagnostic method for early and rapid use for the confirmation of Visceral Leishmaniasis (VL) and applicable to both human and canine reservoir samples would be an important tool to support the fight and control of this disease.

Currently, there are no quality serological tests that can be used for the canine VL diagnosis. In a meta-analysis study conducted (PEIXOTO; DE OLIVEIRA; ROMERO, 2015) it was possible to identify that the antigens used in the main serological methods used for the diagnosis of CVL (ELISA and DPP), Are not highly accurate. This study also highlights the need for improvement, increased quality, and implementation of new tests to diagnose this disease.

The lack of reliable diagnostics creates a large gap in monitoring endemic areas, as much of the demand for testing is directed toward dogs in these regions. Due to this problem, a reliable diagnosis of CVL requires a set of serological and molecular tests (ELISA, IFAT, PCR and qPCR) which is a very costly practice (BOURDEAU et al., 2014). Without a diagnosis and control of the disease in dogs, it is not possible to expect success in its control in humans.

In this regard, it should be clarified that the development of recombinant proteins that bring together several antigenic determinants in a single molecule (chimeric protein) may result in an excellent proposal as it facilitates the standardization of diagnostic tests, and there are already studies indicating that a single molecule containing several antigens could allow a better distribution of the antigenic determinants on the ELISA plate, when compared to using multiple molecules in the same assay (CAMUSSONE et al., 2009).

Pioneering work in the 1990s and more recent studies have highlighted the potential of chimeric proteins for the diagnosis of *L. infantum* infection (BOARINO et al., 2005; FARIA et al., 2015; SOTO et al., 1998). To date, however, the use of these molecules in the clinic, and in particular for the canine VL diagnosis, is still limited and/or has not led to a significant increase in the quality of diagnosis of the disease.

As can be seen, no state-of-the-art document teaches a single tool for the VL diagnosis in humans or dogs. In view of the aforementioned problem in the diagnosis of VL of the prior art, the present invention provides the selection of three recombinant proteins, selected for the best performance in human or canine VL diagnosis and further development of chimeric proteins comprising various antigenic determinants with high sensitivity and specificity.

The advantages of the invention will be evident in the description of the invention provided herein.

SUMMARY OF THE INVENTION

The present invention aims to provide polypeptides for VL diagnostics in humans and dogs.

Polypeptides are in the form of chimeric polypeptide constructs comprising antigenic regions of efficient proteins for the VL diagnosis.

particularly, the present invention relates to the production of synthetic chimeric proteins for the VL diagnosis in humans and dogs. [0056] In a first embodiment, the present invention provides chimeric proteins comprising efficient protein antigenic regions for VL diagnosis.

In a second embodiment, the present invention provides nucleic acid molecules and their degenerate sequences encoding said chimeric proteins.

In a third embodiment, the present invention provides an expression cassette comprising said nucleic acid molecules.

In a fourth embodiment, the present invention provides an expression vector comprising said nucleic acid molecules or said expression cassette.

In a fifth embodiment, the present invention provides a host cell comprising said nucleic acid molecules, said expression cassette or said expression vector.

On a sixth embodiment, the present invention provides a method for producing said chimeric proteins comprising the following steps:

transforming a host cell with the expression vector comprising the aforementioned nucleic acid molecule as defined above, culturing said host cell for the production of the chimeric proteins; and isolating said chimeric proteins from said cell or from the culture medium surrounding said cell.

In a seventh embodiment, the present invention provides a Visceral Leishmaniasis diagnostic composition comprising one or more chimeric proteins as defined above.

In an eighth embodiment, the present invention provides a Visceral Leishmaniasis diagnostic kit comprising one or more chimeric proteins or a composition as defined above.

In a ninth embodiment, the present invention provides the use of one or more chimeric proteins in the Visceral Leishmaniasis diagnosis.

In a tenth embodiment, the present invention provides a method for diagnosing Visceral Leishmaniasis comprising the following steps:

From a human or dog serum sample, contact one or more chimeric proteins with a human or dog serum sample, Detect the chimeric protein/antibody complex formed in the previous step using an immunological detection technique.

DETAILED DESCRIPTION OF THE INVENTION

Figure 1:
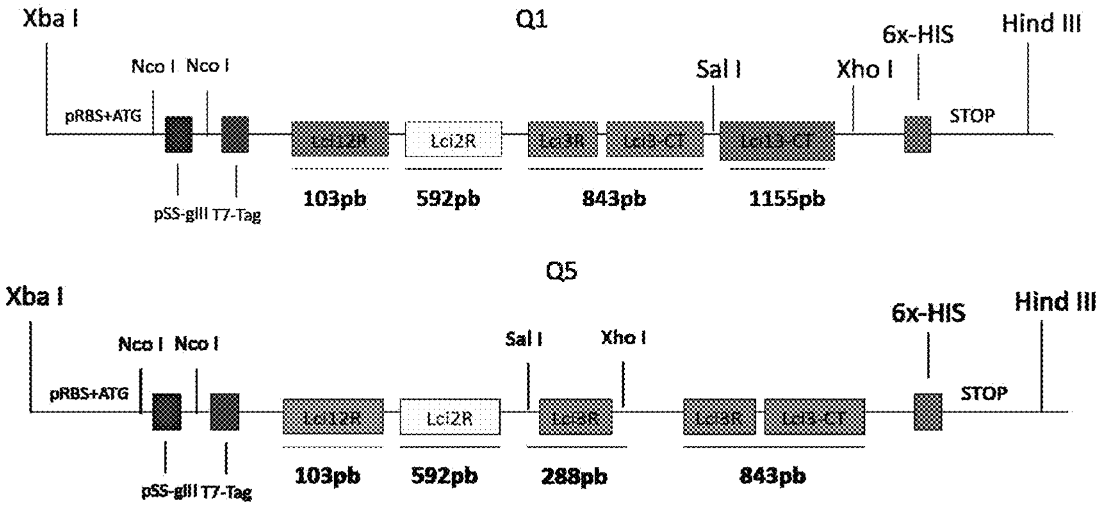
FIG. 1 refers to the schematic representation of the chimeric proteins Q1 and Q5. The complete chimera is represented, showing, in the (Q1) in Q4, the Lci12-2-3-13 regions and, in Q5, the Lci12-2-3 regions flanked by XbaI/HindIII enzyme sites and the SalI/XhoI sites for truncations and the pSS-gIII optimization tag flanked by the NcoI site.

Unless differently defined, all technical and scientific terms used herein have the same meaning as understood by a person skilled in the subject matter to which the invention pertains. The terminology used in describing the invention is intended to describe particular embodiments only, and does not intend to limit the scope of the teachings. Unless otherwise stated, all numbers expressing quantities, percentages and proportions, and other numerical values used in the descriptive report and claims, should be understood as being modified in all cases by the term "about". Thus, unless otherwise stated, the numerical parameters shown in the descriptive report and in the claims are approximations that may vary, depending on the properties to be obtained.

The practice of the present invention will employ, unless otherwise indicated, conventional methods of chemistry, biochemistry, recombinant DNA techniques, and immunology, within the skill of the art. Such techniques are explained fully in the literature. Take a look, e.g. Fundamental Virology, 2nd Edition, vols. I & II (B. N. Fields and D. M. Knipe, eds.) Handbook of Experimental Immunology, Vols. I-IV (D. M. Weir and C. C. Blackwell eds., Blackwell Scientific Publications); T. E. Creighton, Proteins: Structures and Molecular Properties (W.H. Freeman and Company, 1993); A. L. Lehninger, Biochemistry (Worth Publishers, Inc., current edition); Sambrook, et al, Molecular Cloning: A Laboratory Manual (2nd Edition, 1989) Methods In Enzymology (S. Colowick and N. Kaplan eds., Academic Press, Inc.).

The polypeptides of the present invention exhibited reproducibility with respect to sensitivity and specificity. This suggests that the developed proteins can remain stable for long periods of time, maintaining their reactive capacity. It is possible that the composition of the stock buffer may have favored its stability, the use of protease inhibitors, the presence of a denaturing agent in the buffer, or even due to their amino acid sequence. Stable proteins are considered when there is interest for diagnostic application.

As employed throughout the present application, the term "amino acid" denotes the α-amino group that directly or in the form of a precursor can be encoded by a nucleic acid. The individual amino acids are encoded by nucleic acids consisting of three nucleotides, known as codons or suit of bases. Each amino acid is encoded by at least one codon. The fact that the same amino acid is encoded by different codons is known as "degeneracy of the genetic code". The term "amino acid", as used in the present application, denotes the naturally occurring α-amino acids, comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The terms "peptide", "polypeptide" or "protein" can be used interchangeably, and refer to a polymer of amino acids connected by peptide bonds, regardless of the number of amino acid residues constituting this chain. Polypeptides, as used here, include "variants" or "derivatives" thereof, which refer to a polypeptide that includes variations or modifications, for example, substitution, deletion, addition, or chemical modifications in its amino acid sequence with respect to the reference polypeptide. Examples of chemical modifications are glycosylation, PEGlation, PEG alkylation, alkylation, phosphorylation, acetylation, amidation, etc. The polypeptide can be produced artificially from cloned nucleotide sequences using the recombinant DNA technique, or it can be prepared using a known chemical synthesis reaction.

More specifically, the term polypeptide of the present invention may also be understood as antigen, polyantigen or multieptope antigen, which consist of a junction of different epitopes that may or may not be linked by ligands (linkers) flexible or rigid, specific for a single pathogen or for different pathogens.

In a first embodiment, the present invention provides chimeric proteins comprising fractions of native *Leishmania infantum* proteins, which have been generated from antigenic combinations of three of the 13 so-called Lci proteins already described (Lci1 to Lci13), selected for presenting the best results for the human VL diagnosis (Lci2) or canine (Lci3 and Lci12).

Such proteins were generated from chemically synthesized genes that underwent multiple subcloning steps and consisted of the splicing of the same fragments of these three antigenic proteins.

The three proteins selected for the chimeric constructs (Lci2, Lci3 and Lci12) have no sequence homology with each other, but have similar structures, consisting of multiple copies of small motifs (Lci2-39 amino acids; Lci3-14 amino acids; Lci 12-8 amino acids) repeated numerous times and flanked by non-repeating regions, as described (MAGALHÃES et al., 2017; OLIVEIRA et al., 2011).

The selection of the antigenic regions of each Lci included in the chimeric constructs was based on size, solubility, and immunogenic potential criteria. The respective coding sequences were then optimized for expression in *Escherichia coli* and spliced into a sequence, taking into consideration the following parameters: reading phase, codon frequency, secondary mRNA structure, GC content distribution, and restriction sites.

Small spacers were included between the antigenic regions in the chimeric protein aiming to facilitate the folding conditions of the resulting recombinant protein. Optimized sequences at the 5' end of the synthetic genes were also included, as well as in the region encoding the ends of proteins, such as: pRBS-SD1+6AA-ribosome binding site and Shine-Dalgarno sequence; pSS-gIII-N-terminal sequence of a bacteriophage envelope protein to optimize expression; t7 tag peptide-N-terminal sequence to stabilize and optimize expression; ET-6His-polyhistidine sequence (six) introduced at the C-terminal end to allow purification of the protein; and translation termination codon.

Restriction enzyme sites were also added to the synthetic genes at strategic points along the constructs, in order to allow easy modification of these genes, if necessary, by including or excluding some sequences and allowing further manipulation of their structure. These genes gave rise to the chimeric constructs Q1 (SEQ ID NO: 1, 3, and 5) and Q5 (SEQ ID NO: 7) with the predicted sizes of 2845 and 1986 bp (FIG. 1).

These differ in that the Q5 construct includes an additional repetitive segment of the Lci3 protein, absent from the Q1 construct, whereas the original Q1 construct features at the 3' end of the gene a fragment encoding for the C-terminal region of a fourth antigenic protein, Lci13. In possession of the commercially synthesized gene constructs, they were then subcloned into the bacterial expression vector pRSETa, with confirmation of subcloning performed by digestion by the restriction enzyme pair XbaI/HindIII, releasing the DNA fragments of the expected size (FIG. 2) and by sequencing analysis.

For the Q1 construction only (SEQ ID NO: 1) Digests were performed on the fragment cloned into the plasmid pRSETa, using internal restriction sites present only in the synthetic gene, in order to generate truncated variants of this gene where different fragments encoding selected portions of the protein were removed.

The goal of this step was to expand the number of chimeric proteins synthesized in order to see which of the possible alternatives and antigenic combinations enhances protein expression in the prokaryotic system.

A first digestion was performed with the enzyme NcoI that releases a 75 bp fragment in the N-terminal region of the gene encoding the expression optimization peptide pSS-gIII.

After purification and reconnection of the plasmid construct this fragment is lost and the resulting, slightly smaller chimeric gene encodes for a truncated Q1 protein, where this peptide is absent (Q1NN—SEQ ID NO: 4).

Using an equivalent strategy, a second digest was performed from the complete gene (SEQ ID NO: 1) using the SalI/XhoI enzymes. Since the restriction sites for these enzymes are complementary, ligation of the major fragment product of this digestion leads to the production of a chimeric gene (SEQ ID NO: 5) where the 1155 bp fragment encoding for Lci13 (Q1SX—SEQ ID NO: 6).

Figure 2:
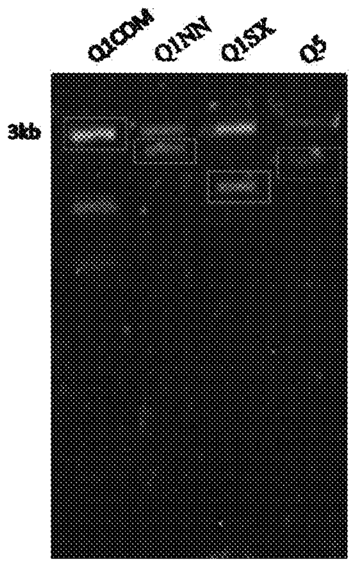
FIG. 2 refers to the confirmation of the subcloning of the chimeric genes. One can observe a 1% Agarose gel showing the genes Q1COM, Q1NN, Q1SX and Q5, by digestion with the enzyme duo XbaI/HindIII, the release of the complete chimeric genes (shown in red) in the expected sizes shown in table 1. Thus confirming the subcloning. The marker used was Ladder 1 Kb plus. Notes: Q1COM, was digested by the enzymes ScaI/XbaI/HindIII, because the insert is the same size as the vector, so additional digestion was performed with ScaI that leads to cleavage of the plasmid into two fragments and allows visualization of the insert as indicated.

FIG. 2 also illustrates the fragments generated after digestion of the plasmids containing the two truncated constructs generated from the chimeric Q1 gene (SEQ ID NO: 1) and the sizes of each are summarized in Table 1.

TABLE 1

| PRIMARY NAME | Insert size (in pb) | Protein size (kDa) |
|---|---|---|
| Q1 | 2845 | 102 |
| Q1NN | 2734 | 99 |
| Q1SX | 1690 | 60 |
| Q5 | 1960 | 98 |

In a second aspect, the invention provides nucleic acid molecules encoding the disclosed chimeric proteins.

The nucleic acid molecules of the present invention are represented, non-limiting, by SEQ ID NO: 1, SEQ ID NO: 3, SEQ ID NO: 5 or SEQ ID NO: 7, or sequences with at least 90% identity to SEQ ID NO: 1, SEQ ID NO: 3, SEQ ID NO: 5, or SEQ ID NO: 7, or their degenerate sequences that encode the same polypeptide.

The term "degenerate nucleotide sequence" denotes a nucleotide sequence that includes one or more degenerate codons when compared to a reference nucleic acid molecule encoding a given polypeptide. Degenerate codons contain different triplets of nucleotides, but encode the same amino acid residue (for example, GAU and GAC both encode Asp).

A subject matter expert would recognize that the degenerations are fully supported based on the information provided in the application and common knowledge of the prior art. For example, the degeneration of the genetic code (that is, different codons can encode the same amino acids) is common knowledge in the technique and the identity of the amino acid encoded by each codon is well established.

Based on information well known and established in the prior art, the subject matter expert is able to identify nucleotide substitutions that do not alter the resulting amino acid sequence. Thus, when in possession of both the nucleotide sequence of a gene and the amino acid sequence of the encoded protein, the subject matter expert will easily identify degenerates that encode the same protein, with the same amino acid sequence.

In a third aspect, the present invention provides an expression cassette comprising the nucleic acid according to the invention. The said cassette is placed under conditions that lead to the expression of the polypeptides of the present invention.

The expression cassette may further comprise sequences necessary for its expression, such as, promoters, enhancer and terminator sequences compatible with the expression system. Furthermore, the expression cassette can comprise spacer sequences, ligand sequences and suitable restriction sites. In addition, the cassette may also comprise a sequence coding for histidine tails.

In a fourth aspect, the present invention provides an expression vector comprising a nucleic acid molecule or an expression cassette according to the invention. Said vector can be used to transform a host cell and allow the expression of the nucleic acid according to the invention in said cell.

Advantageously, the expression vector comprises regulatory elements that enable the expression of a nucleic acid molecule and elements that enable its selection in the host cell according to the invention. The methods for selecting these elements depending on the host cell in which expression is desired, are well known to those versed in the technique and widely described in the literature.

The vectors can be constructed by classical molecular biology techniques, well known to the tech-savvy. Non-limiting examples of expression vectors suitable for expression in host cells are plasmids and viral or bacterial vectors.

In a fifth aspect, the present invention provides a host cell transiently or stably transformed/transfected with the nucleic acid, cassette or vector of the invention. The nucleic acid molecule, cassette or vector may be contained in the cell in the form of an episome or in chromosomal form.

The host cell can be a bacterial cell, yeast, filamentous fungi, protozoa, insects, animal and plant cells.

In a sixth aspect, the present invention provides a method for producing chimeric proteins of the present invention comprising the following steps transforming a host cell with the expression vector comprising said nucleic acid molecule or expression cassette, culturing the said host cell for the production of the chimeric proteins (in vivo expression systems); and isolating said chimeric proteins from said cell or from the culture medium surrounding said cell.

Particularly suitable expression systems include microorganisms, such as bacteria transformed with recombinant DNA expression vectors of bacteriophage, plasmid or cosmid; yeast transformed with yeast expression vectors; insect cell systems infected with virus expression vectors (for example, baculovirus); plant cell systems transformed with virus expression vectors (e.g. cauliflower mosaic virus, CaMV [cauliflower mosaic virus]; tobacco mosaic virus, TMV [tobacco mosaic virus]) or with bacterial expression vectors (e.g. Ti or pBR322 plasmids) or animal cell systems. It is also possible to employ cell-free translation systems to produce the polypeptides of the invention.

The introduction of the nucleic acid molecule, expression cassette, or the vector encoding a recombinant or synthetic protein of the present invention into host cells can be accomplished by methods described in many standard laboratory manuals, such as Davis et al. Basic Methods in Molecular Biology (1986) and Sambrook et al., Molecular Cloning: A Laboratory Manual, Cold Spring Harbor, NY (1989).

Figure 3:
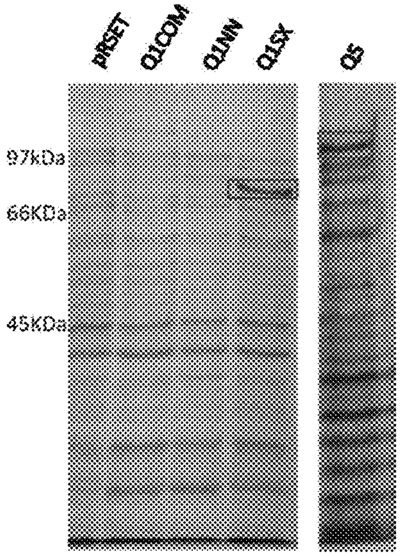
FIG. 3 refers to the expression of the chimeric proteins. An SDS-PAGE gel showing the expression of the chimeric proteins in *Escherichia coli* Rosetta cells at the sizes described in Table 2 can be seen.

In a preferential aspect, the expression of the different recombinant proteins of the present invention was carried out using the plasmid DNA of the generated chimeric constructs, which was transformed into *E. coli* cells and, after the period of growth and expression of the recombinant proteins, Total bacterial extracts from cells expressing the different proteins were fractionated on SDS-PAGE gel (see FIG. 3).

The transformed or transfected host cell described above is then grown in a suitable nutrient medium under conducive conditions that allow the expression of the recombinant proteins of the invention. The medium used to grow the cells can be any conventional medium suitable for growing host cells, such as minimal or complex medium containing appropriate supplements. Suitable media are available from commercial suppliers or can be prepared according to published prescriptions (for example, in the catalogs of the American Type Culture Collection). The proteins of the invention produced by the cells can then be recovered from the cell or culture medium by conventional procedures including separating the host cells from the medium by centrifugation or filtration, precipitating the aqueous protein components from the supernatant or filtrate using a salt, e.g. ammonium sulfate, purification by a variety of chromatographic procedures, for example ion exchange chromatography, exclusion chromatography, hydrophobic interaction chromatography, gel filtration chromatography, affinity chromatography, or similar, depending on the type of polypeptide in question.

The obtained chimeric protein is then purified and biochemically characterized using, for example, methods common to the field of biochemistry, such as HPLC, SDS-PAGE, Western Blotting, pH gradient isoelectric focusing, circular dichroism. By means of these methods, it is possible to determine characteristics such as, for example, the yield of expression of the chimeric protein; the determination of the characteristics of secondary structures, as well as other characteristics whose determination is important for the development of a diagnostic composition for Visceral Leishmaniasis.

In one mode, the transformation of the host cell with the nucleic acid molecule of the present invention is accomplished by means of an expression vector. In a specific mode, the vector is pRSETa and the transformed host cell is *E. coli* Rosetta™ 2. Table 1 illustrates the expected molecular weight for each of the recombinant proteins encoded by the different chimeric genes obtained. Among the four evaluated constructions, only Q1SX (SEQ ID NO: 5) and the Q5 construction (SEQ ID NO: 7) allowed the expression of clearly identifiable bands in the total bacterial extracts.

The host cell culture conditions indicated in step (b) are known to a person skilled in the art. In one embodiment, culturing is performed in LB medium in the presence of an antibiotic, under stirring. In a specific culturing, the antibiotic is ampicillin and chloramphenicol. Culturing can take place at different temperatures for different periods of time. In a specific mode, culturing can be performed for about 4 to about 6 hours at a temperature of about 35° C. to about 37° C. In a preferred embodiment, the culturing is done at 37° C. for 6 hours under stirring.

The production of the chimeric protein referred to in step (b) can be performed with any technique known in the state of the art. In one embodiment, the induction of the chimeric protein expression of the invention is accomplished by adding IPTG to the culture medium, after obtaining adequate optical density.

To confirm the expression of the various truncations of the Q1 protein, the respective bacterial extracts were then subjected to Western Blot assays where the recognition of these proteins by a commercial monoclonal antibody directed against the polyhistidine sequence present in each of the proteins was evaluated.

Figure 4:
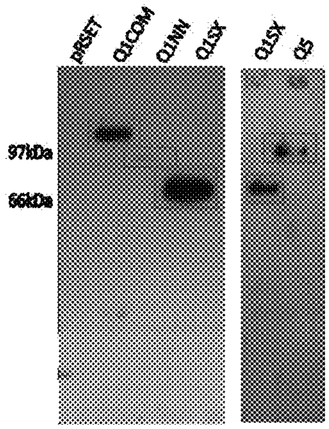
FIG. 4 refers to the western blot of the chimeric proteins. Recognition of the chimeric proteins by the Anti-Histidine monoclonal antibody can be observed. The reaction of the proteins is visualized in red in their predicted sizes.

As shown in FIG. 4, all three Q1 protein constructs were recognized by the monoclonal antibody, confirming their expression, while Q1SX (SEQ ID NO: 5) was expressed at higher levels than the others compatible with its visualization on SDS-PAGE gels.

Figure 5:
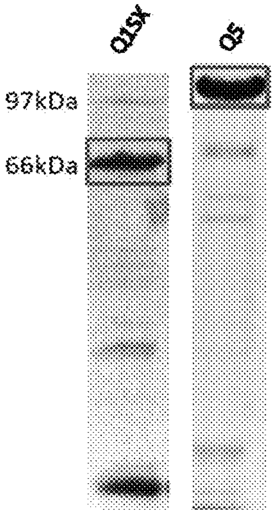
FIG. 5 refers to the purification of the recombinant chimeric proteins Q1SX and Q5 by affinity chromatography. The panel shows the purification profile of the Q1SX and Q5 protein by affinity chromatography, highlighted in red.

Similarly, the Q5 protein (SEQ ID NO: 8) was also recognized by the commercial antibody directed at the polyhistidine sequence. From the expression analysis, *E. coli* cultures expressing Q1SX and Q5 proteins were expanded for large scale expression of these proteins and purification by affinity chromatography on Nickel resin. FIG. 5 shows representative SDS-PAGE gels of the purification of the Q1SX and Q5 proteins.

The purified Q1SX and Q5 proteins were quantified by comparison with defined amounts of BSA on SDS-PAGE and used in ELISA assays aiming to evaluate their potential in the diagnosis of human and canine VL. Each protein was then evaluated with human sera from individuals proven to be infected with *L. infantum*, sera from healthy controls, sera from proven VL infected dogs and their respective healthy controls.

The isolation of the chimeric protein referred to in step (c) can be performed with any technique known in the state of the art. In an embodiment, purification is achieved by chromatography techniques. In a specific embodiment, purification is performed by nickel resin affinity chromatography. Non-limiting examples include the affinity chromatography method, ion exchange, other affinity or adsorption methods, ion pair, reversed phase, and molecular exclusion.

In a seventh aspect, the invention provides a composition, comprising one or more of the chimeric proteins according to the present invention.

In a particular aspect, the composition is used as a reagent for the Visceral Leishmaniasis diagnosis.

In an eighth aspect, the invention provides a Visceral Leishmaniasis diagnostic kit comprising one or more chimeric proteins or a composition as defined in the present invention.

Optionally, the kit also includes instructions for use. [00124] Additionally, the kit may further comprise a means for detecting the antigen/antibody complex, which may comprise a signal generator, capable of generating a detectable signal.

The detection means can be those known in the technique. A non-limiting example of the detection means may be a conjugate comprised of an antibody coupled to a signal generating compound capable of generating a detectable signal.

In a ninth aspect, the invention provides the use of said chimeric proteins in the Visceral Leishmaniasis diagnosis.

In a tenth aspect, the invention provides a method for diagnosing Visceral Leishmaniasis comprising detecting the chimeric protein/antibody complex by using an immunological detection technique from a human or dog serum sample.

Figure 6:
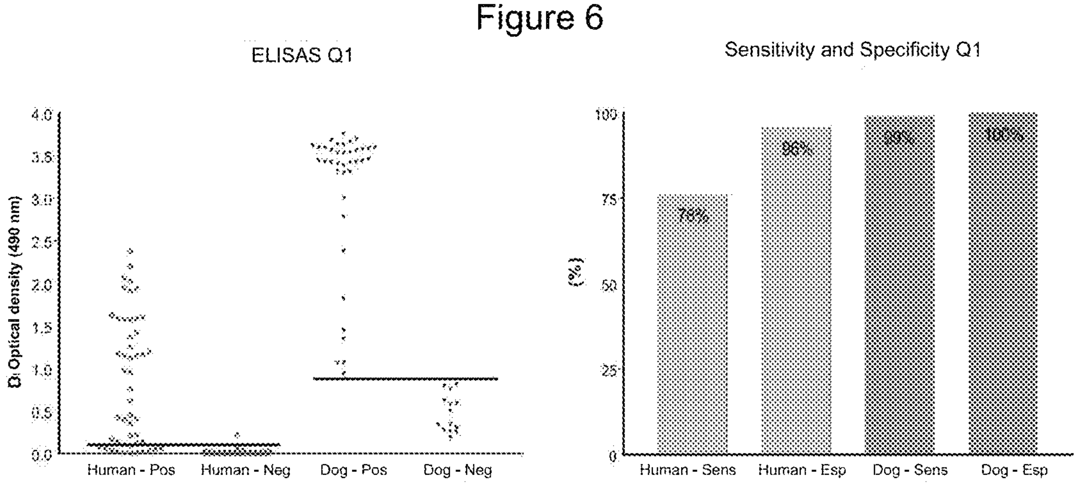
FIG. 6 refers to the indirect ELISA of the Q1SX chimeric protein with the VL sera. The scatterplots and bar graphs show the sensitivity and specificity of the 50 human and 40 dog sera positive for VL against the Q1 chimeric protein. The horizontal line represents the cutoff of the reaction.

The evaluation of the chimeric proteins of the present invention has demonstrated that, from the results of the ELISA of the chimeric protein Q1 with sera from humans and dogs, it presented a sensitivity for human sera of (76%) and specificity of (100%), however, results with sera from dogs showed a sensitivity of (99%) and specificity of (100%) shown in FIG. 6.

Figure 7:
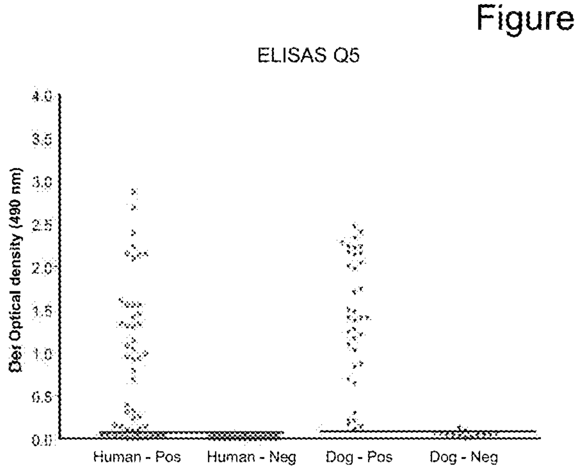
FIG. 7 refers to the indirect ELISA of the Q5 chimeric protein with the VL sera. The scatterplots and bar graphs show the sensitivity and specificity of the 50 human and 40 dog sera positive for VL against the Q5 chimeric protein. The scatter plot shows the human and dog sera against Q5. The horizontal line represents the cutoff of the reaction.
Figure 7:
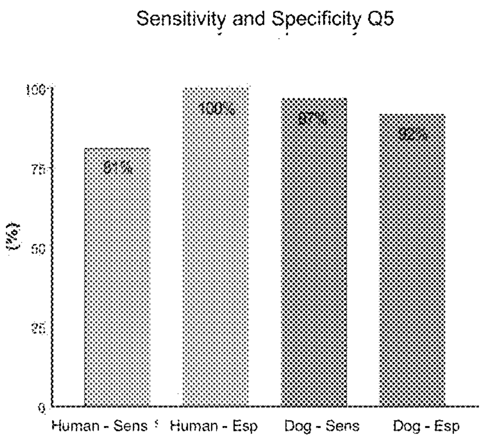

The results of the Q5 chimeric protein ELISA showed a sensitivity for human sera of 81%, while the results with dog sera maintained a sensitivity of 99% (FIG. 7).

Figure 8:
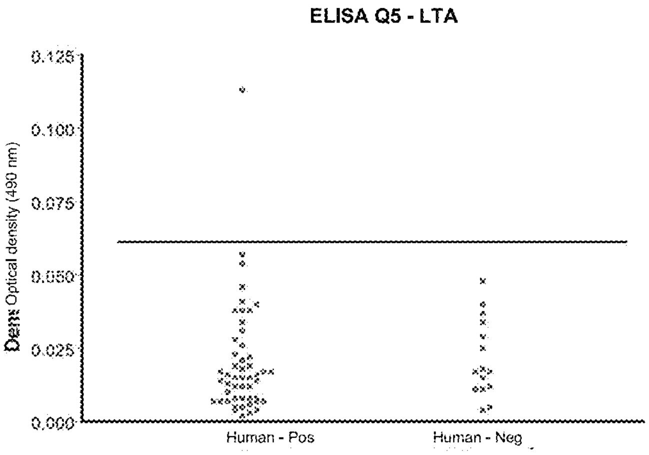
FIG. 8 refers to the indirect ELISA of the Q5 chimeric protein with LTA sera. The scatter plots show the cross-reaction of the 50 human sera positive for ATL against the Q5 chimeric protein. The horizontal line represents the cutoff of the reaction.

Based on the best results obtained for the Q5 protein, said protein was used in new ELISA assays to assess its cross recognition with sera from patients with tegumentary leishmaniasis. The results with these sera showed a nonspecific reaction of 8% (FIG. 8).

Figure 9:
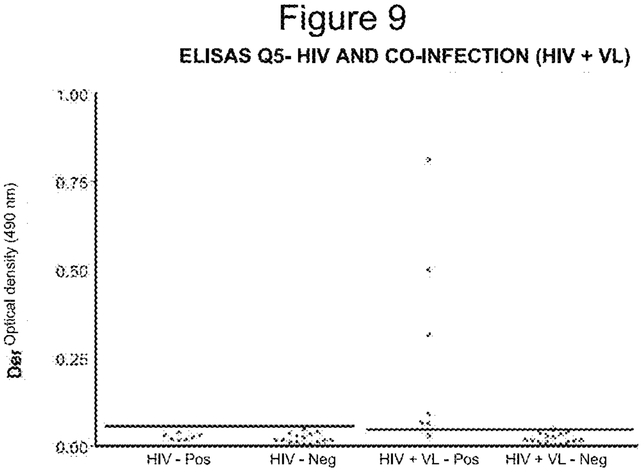
FIG. 9 refers to the indirect ELISA of the Q5 chimeric protein with HIV and HIV+/VL+ Coinfected sera. Scatter plots show the cross-reactivity of HIV-positive human sera and the sensitivity and specificity and of co-infected (VL+HIV) against the chimeric Q5 protein. The scatter plot shows the positive and negative human sera against Q5. The horizontal line represents the cutoff of the reaction.

Sera from patients co-infected with VL and HIV were then evaluated, showing 98% sensitivity and 100% specificity (shown in FIG. 9) and no reaction with HIV-positive patients only. Table 2 shows the results of all analyzes with sera from the groups described above with Q5 and Q1SX protein, showing the sensitivity, specificity and amount of sera evaluated.

TABLE 2

| Serum Type | Sensitivity | Specificity | Quantity Serum Pos |
|---|---|---|---|
| Human Piauí (Q5) | 82% | 100% | 50 |
| Human Piauí (Q1) | 72% | 96% | 50 |
| Coinfected Lv+/HIV+ (Q5) | 86% | 100% | 7 |
| Human LTA (Q5) | 2% | 100% | 50 |
| Humans HIV+/VL− (Q5) | 0% | 100% | 7 |
| Bahia Dogs (Q5) | 99% | 100% | 37 |
| Bahia Dogs (Q1) | 99% | 100% | 37 |

Results of the Q1 and Q5 protein ELISA showing the amount of sera used in each test group and the sensitivity and specificity shown in each group as well. Divided into Dogs and Humans. The negative sera were also tested to calculate the values.

EXAMPLES

Example 1

Bioinformatics Methods, Chemical Synthesis and Subcloning of Chimeric Genes

The prediction of the presence of linear B-cell epitopes in the sequences of selected proteins (Lci2, Lci3 and Lci12) was performed by the program BCPred12 (EL?MANZALAWY; DOBBS; HONAVAR, 2008). The sequences of the chimeric genes optimized for the expression in *Escherichia coli* were designed using the Gendesigner program (WELCH et al., 2011) and their commercial synthesis carried out by GenScript companies (GenScript, Piscataway, New Jersey, USA) (Q1 protein) and Thermo (Life Tech, Sao Paulo, Brazil). (Q5 protein).

These genes were delivered already cloned into the commercial vector pUC57 flanked by restriction sites for the enzymes XbaI/HindIII. For subcloning into the bacterial expression vector, pRSETa (Thermo Life Tech, Sao Paulo, Brazil), the chimeric genes were recovered by double digestion with the restriction enzymes XbaI/HindIII and subcloned into the same sites of the pRSETa vector.

After the first subcloning of the Q1 gene into the pRSETa vector two truncation reactions of this gene were performed. The first, from digestion with the enzyme NcoI, which led to the excision of the fragment encoding the pSS-gIII peptide, and the second with the SalI/XhoI enzyme pair, excising the fragment encoding the C-terminal region of the Lci13 protein. All final constructs were confirmed by digestion with restriction enzymes and sequencing.

Example 2

Expression and Purification of Recombinant Proteins

For the expression of the chimeric protein, plasmid constructs derived from the pRSETa vector were transformed into competent *E. coli* Rosetta™ 2 cells (Merck Millipore) followed by selection on LB medium (Luria Bertani) ampicillin-supplemented solid (100 μg/ml) and chloramphenicol (34 μg/ml) at 37° C.

Clones of the transformed cells were grown in liquid LB medium with the same concentrations of antibiotics and induction of expression of the recombinant proteins performed by adding IPTG to a final concentration of 0.1 mM, at an optical density (D.O) from 0.6 to 0.8 at 600 nm.

The result was visualized using a polyacrylamide gel (SDS-PAGE 15%) after staining the gel with Comassie Blue R-250. To obtain recombinant proteins, cell pellets obtained after the induction were resuspended in 20 mL of lysis buffer and equilibrated (100 mM sodium phosphate, 10 mM Tris, 8 M Urea, 20 mM imidazole—pH 8.0) and solubilized by ultrasonication in 5 pulses of 30 seconds at intervals of 1 minute at 4° C.

After centrifugation at 5000 rpm for 10 minutes, protein purification was performed by incubation with Ni-NTA agarose resin (Qiagen) followed by washes in the same buffer and in denaturing buffer at pH 6.0 (100 mM sodium phosphate, 10 mM Tris, 8 M Urea, 30 mM imidazole) and elution in denaturing buffer at pH 4.5 at 1 M imidazole. Aliquots were evaluated on SDS-PAGE gels as described.

Example 3

Western Blot Assays

For Western-blot assays chimeric proteins were fractionated on 15% SDS-PAGE gels and transferred to PVDF membranes (Immobilon-P Millipore®) which were blocked in TBS buffer (20 mM Tris, 500 mM NaCl, pH7,5) supplemented with 5% skim milk and 1% Tween-20.

The membranes were then incubated with the antibodies/sera against the target proteins at final dilutions of 1:3000 and 1:1000 in TBS buffer with 5% milk and 1% Tween-20. After washing with 1% TBS/Tween-20, a new incubation with rabbit anti IgG was performed, labeled with peroxidase, (Jackson Immunoresearch Laboratories), diluted 1:10000 in TBS buffer with 5% milk and 1% Tween-20.

After further washing, the membranes were revealed in a solution of 1.2 mM luminol, 0.4 mM iodophenol and 0.03% hydrogen peroxide for 2 minutes. These membranes were then dried and exposed to autoradiography film for 1 and 5 minutes, followed by developing the film.

Example 4

Human Sera Used

Initially, a panel of human sera consisting of two distinct sera groups was assembled. The first group was composed of 50 sera obtained from the control group in the serum library of the Laboratory of Virology and Experimental Therapy (LAVITE) of the JAM, set up for the yellow fever vaccine project. These sera come from healthy individuals living in a non-endemic area for visceral leishmaniasis (urban area of the city of Recife) and were kindly provided by Dr. Rafael Dhália.

The second group consisted of 50 sera from patients with visceral leishmaniasis with clinical and laboratory diagnosis (confirmed by parasitological examination) This information was kindly provided by Dr. Carlos Henrique Costa, from the Federal University of Piauí.

All human sera were collected after approval for use, by appropriate ethics committees, as described below: the use of serum from VL patients was approved by the ethics committee of the Federal University of Piauí (0116/2005); the sera from the negative controls were included in a study approved by the ethics committee of the Ministry of Health (25000.119007/2002-03).

Sera from patients with cutaneous leishmaniasis, included in project CAEE 0014.0.095.000-05, approved by the ethics committee of CPqAM-FIOCRUZ, were also used (Mar. 8, 2008).

Finally sera from patients with coinfection (HIV/VL) and the sera from patients with HIV only, also evaluated in this proposal, were provided by Dr. Zulma Medeiros, from a project approved by the ethics committee of the Centro de Pesquisas Aggeu Magalhães—FIOCRUZ (CAEE: 53495816.0.0000.5190).

Example 5

Dog Serums Used

About one hundred domesticated or stray dogs were studied from an endemic area of visceral leishmaniasis in Jequié-BA.

Blood samples were collected, and from there, aliquots of serum were obtained and stored at −20° C. For some of these animals an aspiration puncture of the spleen was performed and the aspirate used for culture and detection of *Leishmania*, according to the method previously described (BARROUIN-MELO et al., 2006).

We also used 90 sera from dogs with VL provided in partnership with Dr. Valeria Pereira. All dogs were treated according to the guidelines for animal experimentation of the Oswaldo Cruz Foundation. [00151] The use of the dog sera in this study was approved by the Ethics Committee on Animal Use (CPqGM-FIOCRUZ, Ceua, protocol N.040/2005 and CPqAM-FIOCRUZ, Ceua, protocol 27/2016).

Example 6

Indirect Enzyme Immunoassay

After quantification, the recombinant proteins were used for sensitization of microtiter plates, diluted in carbonate-bicarbonate buffer (NaCO3, 0.05 M; pH 9.6), for a concentration of 400 ng (1 ?g for the total extract of the *Leishmania infantum* parasite, used as a reaction control) per well with a volume of 100 ?1 per well, and kept for 16 hours at 4° C. in a humid chamber.

After washes with PBS (NaCl 137 mM, KCl 2.7 mM, Na2HPO4 10 mM, KH2PO4 1.8 mM) blocking was performed with PBS plus 10% skim milk, followed by further washing with PBS plus 0.05% Tween-20. Incubation with the human and canine sera was then carried out, diluted in PBS Tween-20 with 10% milk at dilutions of 1:2500 and 1:900, respectively.

Washing and incubation steps were again followed with the conjugates, anti-Human IgG or anti-Canine IgG linked to peroxidase, for 1 hour at room temperature in a humid chamber, in dilutions of 1:10000 and 1:1200, respectively.

After further washing, development was carried out in citrate-phosphate buffer (Na2HPO4, C6H8O7, 0.1 M, pH:5.0) in the presence of the chromogen OPD (Orthophenylenediamine) in a 0.01% concentration (300 μl) and hydrogen peroxide (in a 4% concentration, 3 μl) in a darkroom for 30 minutes, and the reaction was stopped with sulfuric acid (H2SO4 at 2.5 M). The reading was performed in a 490 nm filter in the Benchmark Plus Microplate Manager 5.2 (BIO-RAD).

Example 7

Statistical Analysis of the Indirect ELISA Results

The parameters of sensitivity, specificity, positive and negative predictive value and confidence interval were estimated using MedCalc software (version 12.3) (MedCalc Software, Ostend, Belgium).

For the association between the variables and their determinants, the chi-square test was used in a double-entry table (2×2) relating the diagnosis of the disease and the test result.

Sensitivity is given by the percentage of positives detected by the test among individuals known to be ill (positive parasitological), and specificity, by the percentage of negatives among non-diseased individuals.

The scatter plot was obtained using the GraphPad Prism software (GraphPad Prism version 6.00 for Windows, GraphPad Software, La Jolla California USA).

REFERENCES

AKHOUNDI, M. et al. A Historical Overview of the Classification, Evolution, and Dispersion of *Leishmania* Parasites and Sandflies. PLoS Neglected Tropical Diseases, v. 10, n. 3, p. 1-40, 2016.

AVLAR, J. et al. Leishmaniasis worldwide and global estimates of its incidence. PLoS ONE, v. 7, n. 5, 2012.

BARROUIN-MELO, S. M. et al. Can spleen aspirations be safely used for the parasitological diagnosis of canine visceral leishmaniosis? A study on asymptomatic and polysymptomatic animals. Veterinary Journal, v. 171, n. 2, p. 331-339, 2006.

BOARINO, A. et al. Development of Recombinant Chimeric Antigen Expressing Immunodominant B Epitopes of *Leishmania infantum* for SeroVisceral Leishmaniasis diagnosis. Clinical and Vaccine Immunology, v. 12, n. 5, p. 647-653, 2005.

BOELAERT, M. et al. A comparative study of the effectiveness of diagnostic tests for visceral leishmaniasis. Am. J. Trop. Med. Hyg., v. 70, n. 1, p. 72-77, January 2004.

BOELAERT, M. et al. Rapid tests for the diagnosis of visceral leishmaniasis in patients with suspected disease. Cochrane. Database. Syst. Rev., v. 6, n. 1469-493X (Electronic), p. CD009135, 2014.

BOURDEAU, P. et al. Management of canine leishmaniosis in endemic SW European regions: a questionnaire-based multinational survey. Parasites & Vectors, v. 7, n. 1, p. 110, 2014.

CAMPOS, R. M. et al. Distinct mitochondrial HSP70 homologues conserved in various *Leishmania* species suggest novel biological functions. Molecular and Biochemical Parasitology, v. 160, n. 2, p. 157-162, 2008.

CAMUSSONE, C. et al. Comparison of recombinant *Trypanosoma cruzi* peptide mixtures versus multiepitope chimeric proteins as sensitizing antigens for immunodiagnosis. Clinical and Vaccine Immunology, v. 16, n. 6, p. 899-905, 2009.

CAÑAVATE, C. et al. Evaluation of two rK39 dipstick tests, direct agglutination test, and indirect fluorescent antibody test for diagnosis of visceral leishmaniasis in a new epidemic site in highland Ethiopia. American Journal of Tropical Medicine and Hygiene, v. 84, n. 1, p. 102-106, 2011. [00170] CHAPPUIS, F. et al. A meta-analysis of the diagnostic performance of the direct agglutination test and rK39 dipstick for visceral leishmaniasis. BMJ (Clinical research ed.) v. 333, n. 7571, p. 723, 2006.

CHAPPUIS, F. et al. Visceral leishmaniasis: what are the needs for diagnosis, treatment and control? Nat. Rev. Microbiol., v. 5, n. 1740-1534 (Electronic) p. 873-882, nov. 2007.

DE RUITER, C. M. et al. Molecular tools for diagnosis of visceral leishmaniasis: systematic review and meta-analysis of diagnostic test accuracy. J. Clin. Microbiol., v. 52, n. 1098-660X (Electronic), p. 3147-3155, September 2014.

EL-MANZALAWY, Y.; DOBBS, D.; HONAVAR, V. Predicting linear B-cell epitopes using string kernels. Journal of Molecular Recognition, v. 21, n. 4, p. 243-255, jul. 2008.

FARIA, A. R. et al. Novel Recombinant Multiepitope Proteins for the Diagnosis of Asymptomatic *Leishmania infantum*-Infected Dogs. PLoS Neglected Tropical Diseases, v. 9, n. 1, p. 13-16, 2015.

FRAGA, D. B. M. et al. A multicentric evaluation of the recombinant *Leishmania infantum* antigen-based immunochromatographic assay for the serodiagnosis of canine visceral leishmaniasis. Parasit. Vectors, v. 7, n. 1756-3305 (Electronic), p. 136, 2014.

FRAGA, D. B. M. et al. The Rapid Test Based on *Leishmania infantum* Chimeric rK28 Protein Improves the Diagnosis of Canine Visceral Leishmaniasis by Reducing the Detection of False-Positive Dogs. PLoS Neglected Tropical Diseases, v. 10, n. 1, p. 1-11, 2016.

GOMES, Y. M. et al. Diagnosis of canine visceral leishmaniasis: Biotechnological advances. Veterinary Journal, v. 175, n. 1, p. 45-52, 2008.

KAMHAWI, S. Phlebotomine sand flies and *Leishmania* parasites: friends or foes? Trends in Parasitology, v. 22, n. 9, p. 439-445, 2006.

KAYE, P.; SCOTT, P. Leishmaniasis: complexity at the host-pathogen interface. Nature reviews. Microbiology, v. 9, n. 8, p. 604-615, 2011.

MAGELLAN, F. B. et al. Evaluation of a new set of recombinant antigens for the serological diagnosis of human and canine visceral leishmaniasis. PLoS ONE, v. 12, n. 9, p. e0184867, 2017.

METTLER, M. et al. Evaluation of enzyme-linked immunosorbent assays, an immunofluorescent-antibody test, and two rapid tests (immunochromatographic-dipstick and gel tests) for serological diagnosis of symptomatic and asymptomatic *Leishmania* infections in dogs. J. Clin. Microbiol., v. 43, n. 0095-1137 (Print) p. 5515-5519, nov. 2005.

MURRAY, H. W. et al. Advances in leishmaniasis. Lancet, v. 366, n. 1474-547X (Electronic) p. 1561-1577, October 2005.

NOLI, C.; SARIDOMICHELAKIS, M. N. An update on the diagnosis and treatment of canine leishmaniosis caused by *Leishmania infantum* (syn. *L. chagasi*). The Veterinary Journal, v. 202, n. 3, p. 425-435, 2014.

OLIVEIRA, G. G. et al. Characterization of novel *Leishmania infantum* recombinant proteins encoded by genes from five families with distinct capacities for serodiagnosis of canine and human visceral leishmaniasis. Am. J. Trop. Med. Hyg., v. 85, n. 1476-1645 (Electronic), p. 1025-1034, December 2011.

PACE, D. Leishmaniasis. Journal of Infection, v. 69, n. S1, p. S10-S18, 2014.

PALTRINIERI, S. et al. Laboratory tests for diagnosing and monitoring canine leishmaniasis. Veterinary Clinical Pathology, v. 45, n. 4, p. 552-578, 2016.

PATTABHI, S. et al. Design, development and evaluation of rK28-based point-of-care tests for improving rapid diagnosis of visceral leishmaniasis. PLoS Neglected Tropical Diseases, v. 4, n. 9, 2010.

PEIXOTO, H. M.; DE OLIVEIRA, M. R. F.; ROMERO, G. A. S. Serological diagnosis of canine visceral leishmaniasis in Brazil: systematic review and meta-analysis. Tropical Medicine & International Health, v. 20, n. 3, p. 334-352, 2015.

QUINNELL, R. J. et al. Evaluation of rK39 rapid diagnostic tests for canine visceral leishmaniasis: longitudinal study and meta-analysis. PLoS. Negl. Trop. Dis., v. 7, n. 1935-2735 (Electronic)

QUINNELL, R. J.; COURTENAY, O. Transmission, reservoir hosts and control of zoonotic visceral leishmaniasis. Parasitology, v. 136, n. 14, p. 1915, 2009.

READY, P. D. Biology of Phlebotomine Sand Flies as Vectors of Disease Agents. Annual Review of Entomology, v. 58, n. 1, p. 227-250, 2013.

SARIDOMICHELAKIS, M. N. Advances in the pathogenesis of canine leishmaniosis: Epidemiologic and diagnostic implications. Veterinary Dermatology, v. 20, n. 5-6, p. 471-489, 2009.

SINGH, O. P.; SUNDAR, S. Developments in Diagnosis of Visceral Leishmaniasis in the Elimination Era. v. 2015, 2015.

SINGH, S. et al. Diagnostic and prognostic value of K39 recombinant antigen in Indian leishmaniasis. J. Parasitol., v. 81, n. 0022-3395 (Print) p. 1000-1003, dec. 1995.

SOTO, M. et al. Multicomponent chimeric antigen for serodiagnosis of canine visceral leishmaniasis. Journal of Clinical Microbiology, v. 36, n. 1, p. 58-63, 1998.

SRIVASTAVA, P. et al. Diagnosis of visceral leishmaniasis. Trans. R. Soc. Trop. Med. Hyg., v. 105, n. 1878-3503 (Electronic), p. 1-6, jan. 2011.

SRIVASTAVA, S. et al. Possibilities and challenges for developing a successful vaccine for leishmaniasis. Parasites & Vectors, v. 9, n. 1, p. 277, 2016.

SRIVIDYA, G. et al. Diagnosis of visceral leishmaniasis: developments over the last decade. Parasitol. Res., v. 110, n. 1432-1955 (Electronic), p. 1065-1078, March 2012.

SUNDAR, S. et al. Rapid accurate field diagnosis of Indian visceral leishmaniasis. Lancet, v. 351, n. 9102, p. 563-565, 1998.

SUNDAR, S.; RAI, M. Laboratory diagnosis of visceral leishmaniasis. Clin. Diagn. Lab Immunol., v. 9, n. 1071-412X (Print) p. 951-958, September 2002.

WELCH, M. et al. Designing genes for successful protein expression. 1. ed. [s.1.] Elsevier Inc., 2011. v. 498

The invention claimed is:

1. A chimeric protein comprising an amino acid sequence with at least 90% sequence identity with the sequence selected from the group consisting of SEQ ID NO: 2, SEQ ID NO: 4, SEQ ID NO: 6 or SEQ ID NO: 8.

2. A nucleic acid molecule, selected from the group comprising:

a nucleotide sequence with at least 90% sequence identity with the sequence selected from the group consisting of SEQ ID NO: 1, SEQ ID NO: 3, SEQ ID NO: 5 and SEQ ID NO: 7; and nucleotide sequences encoding one of the same amino acid sequences as defined by SEQ ID NO: 2, 4, 6 and 8, respectively.

3. The nucleic acid molecule according to claim 2, further comprising at least one sequence selected from the group consisting of:

pRBS-SD1+6AA, ribosome binding site and Shine-Dalgarno sequence, pSS-gIII, t7 tag peptide, ET-6His; and translation termination codon.

4. An expression cassette, comprising the nucleic acid molecule according to claim 2, operationally linked to a promoter and a transcription terminator.

5. An expression vector, comprising the nucleic acid molecule whose sequence is selected from the group consisting of SEQ ID NO: 1, SEQ ID NO: 3, SEQ ID NO: 5 or SEQ ID NO: 7 and its degenerate sequences, or the expression cassette, according to claim 4.

6. A host cell, comprising:

the nucleic acid molecule whose sequence is selected from the group consisting of SEQ ID NO: 1, SEQ ID NO: 3, SEQ ID NO: 5, SEQ ID NO: 7 and degenerate sequences thereof, or the expression cassette, according to claim 4.

7. The host cell according to claim 6, wherein the nucleic acid molecule is the expression cassette according to claim 4 in an expression vector.

8. A method for the production of chimeric proteins, comprising the following steps:

(a) transforming a host cell with an expression vector comprising the nucleic acid molecule whose sequence is selected from the group consisting of SEQ ID NO: 1, SEQ ID NO: 3, SEQ ID NO: 5, SEQ ID NO: 7 and degenerate sequences thereof, (b) culturing the host cell to produce the chimeric proteins; and (c) isolating the chimeric proteins from said cell or from the culture medium surrounding said cell.

9. A composition for Leishmaniasis diagnosis, comprising one or more chimeric proteins, according to claim 1, wherein the chimeric protein comprises the amino acid sequence selected from the group consisting of SEQ ID NO: 2, SEQ ID NO: 4, SEQ ID NO: 6 and SEQ ID NO: 8.

10. The composition according to claim 9, wherein the diagnosis is performed on samples from dogs or humans.

11. A Leishmaniasis Diagnostic Kit, comprising one or more chimeric proteins according to claim 1 or a composition for Leishmaniasis diagnosis, comprising one or more chimeric proteins, according to claim 1, wherein the chimeric protein of the kit and composition comprises the sequence selected from the group consisting of SEQ ID NO: 2, SEQ ID NO: 4, SEQ ID NO: 6 and SEQ ID NO: 8.

12. The kit according to claim 11, further comprising instructions for use.

13. The kit according to claim 11, further comprising a means for detecting an antigen/antibody complex, which comprises a signal generator, capable of generating a detectable signal.

14. The kit according to claim 11, wherein the diagnosis is performed on samples from dogs or humans.

15. A Leishmaniasis in vitro diagnostic method, comprising the following:

(a) providing one or more chimeric proteins according to claim 1 or a composition for Leishmaniasis diagnosis, comprising one or more chimeric proteins according to claim 1 with a biological sample to be tested from a human or a dog, wherein the chimeric protein according to claim 1 and the composition for Leishmaniasis diagnosis comprises the amino acid sequence selected from the group consisting of SEQ ID NO: 2, SEQ ID NO: 4, SEQ ID NO: 6 and SEQ ID NO: 8;

(b) contacting the one or more chimeric proteins or said composition with the biological sample to be tested for sufficient time, under sufficient conditions for the formation of antibody/antigen complexes; and (c) detecting an antibody/antigen complex formed in step (b) by means of a detection technique capable of generating a detectable signal in the presence of the antibody/antigen complex.

16. The method according to claim 15, wherein the biological sample is selected from the group comprising saliva, urine, serum or blood.

* * * * *